United States Patent [19]

Altermatt et al.

[11] Patent Number: 5,263,475
[45] Date of Patent: Nov. 23, 1993

[54] INHALER

[75] Inventors: Daniel Altermatt, Münchenstein, Switzerland; Hanspeter Hilpert, Rheinfelden/Nollingen, Fed. Rep. of Germany; Satish C. Khanna, Bottmingen, Switzerland; Werner F. Dubach, Maur, Switzerland; Anton Spaltenstein, Bassersdorf, Switzerland

[73] Assignee: Ciba-Geigy Corp., Ardsley, N.Y.

[21] Appl. No.: 853,460

[22] Filed: Mar. 18, 1992

[30] Foreign Application Priority Data

Mar. 21, 1991 [DE] Fed. Rep. of Germany ............... 91810195[U]
Aug. 28, 1991 [CH] Switzerland ............... 2515/91

[51] Int. Cl.$^5$ ............................................. A61M 15/00
[52] U.S. Cl. ........................... 128/203.15; 128/203.19; 128/203.23
[58] Field of Search ............ 128/203.12, 203.21, 128/203.23, 202.21, 203.19, 200.24, 200.23, 203.15; 604/58; 222/510, 319, 336, 494

[56] References Cited

U.S. PATENT DOCUMENTS

| | | | |
|---|---|---|---|
| 2,581,267 | 1/1952 | Majewski | 222/336 X |
| 3,615,250 | 10/1971 | Vernon | 128/202.26 X |
| 3,823,853 | 7/1974 | Alden | 22/361 |
| 4,098,273 | 7/1978 | Glenn | 604/58 X |
| 4,117,844 | 10/1978 | James | 128/203.15 |
| 4,274,403 | 6/1981 | Struve | 128/203.15 |
| 4,338,931 | 7/1982 | Cavazza | 128/203.15 |
| 4,380,534 | 4/1983 | Fukui | 424/38 |
| 4,817,822 | 4/1989 | Rand | 222/38 |
| 4,884,565 | 12/1989 | Cocozza | 128/203.21 |
| 5,032,609 | 7/1991 | Skidmore | 514/445 |
| 5,033,463 | 7/1991 | Cocozza | 128/203.21 |
| 5,113,855 | 5/1992 | Newhouse | 128/203.12 |
| 5,118,494 | 6/1992 | Schultz | 424/45 |

FOREIGN PATENT DOCUMENTS

| | | | |
|---|---|---|---|
| 518379 | 11/1955 | Canada | 128/203.15 |
| 77694 | 6/1954 | Denmark | 604/58 |
| 2705297 | 8/1978 | Fed. Rep. of Germany | 604/58 |
| 2926659 | 1/1981 | Fed. Rep. of Germany | 128/203.12 |
| 3823535 | 7/1988 | Fed. Rep. of Germany . | |
| 4004904 | 9/1990 | Fed. Rep. of Germany | 128/203.15 |
| 48787 | 1/1983 | Taiwan . | |
| 115093 | 6/1989 | Taiwan . | |
| 1577796 | 7/1990 | U.S.S.R. | 128/203.15 |
| 1630834 | 2/1991 | U.S.S.R. | 604/58 |
| 2165159 | 4/1986 | United Kingdom | 128/203.15 |
| 2191032 | 12/1987 | United Kingdom . | |
| 9106333 | 5/1991 | World Int. Prop. O. | 604/58 |
| 9113646 | 9/1991 | World Int. Prop. O. | 604/58 |

OTHER PUBLICATIONS

European Search Report dated Dec. 4, 1992.

Primary Examiner—Edgar S. Burr
Assistant Examiner—Eric P. Raciti
Attorney, Agent, or Firm—Irving M. Fishman; Karen G. Kaiser; Barbara J. Ikeler

[57] ABSTRACT

An inhaler for introducing a metered amount of solids, for example pharmaceutically active powders, into a stream of air drawn in by a user comprises a storage chamber into which a metering rod extends. The metering rod is provided with a metering recess which fixes the amount of solids to be mixed with the air stream. The storage chamber and the metering rod are movable relative to each other in such a manner that in a first relative position of the metering rod and the storage chamber the metering recess of the metering rod is located in the storage chamber, where it is filled with solids, and in a second relative position it is located in the air channel, where the solids are mixed with the air stream. The axial relative movement can be brought about by the rotation of two housing parts over sloping surfaces.

28 Claims, 16 Drawing Sheets

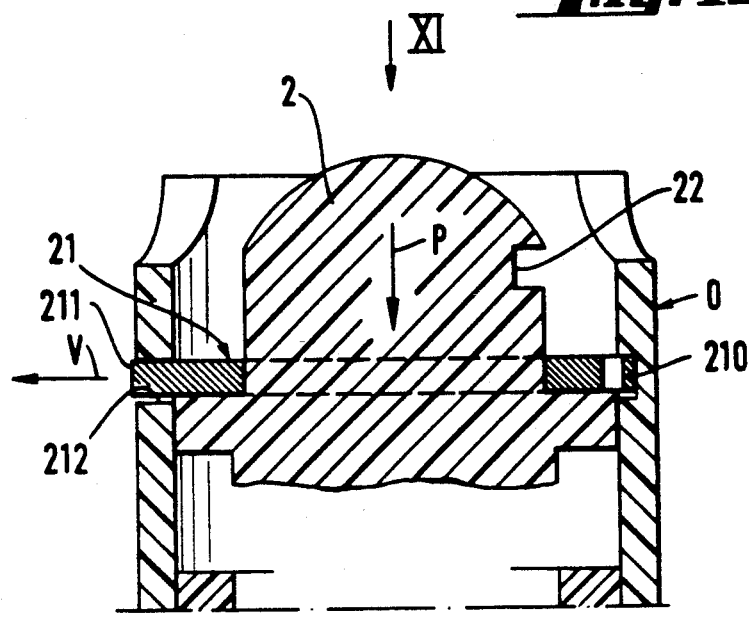
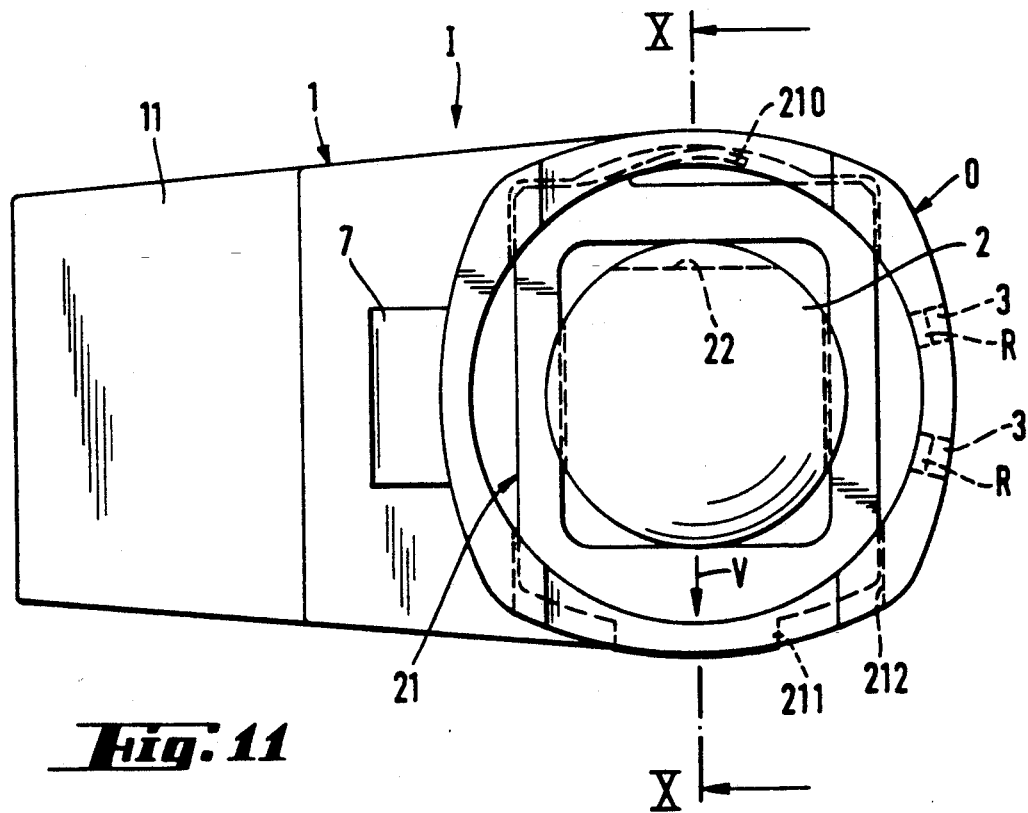

INHALER

BACKGROUND OF THE INVENTION

The invention relates to an inhaler for introducing a metered amount of solids into a stream of air drawn in by a user.

Solids inhalers are nowadays obtainable in large numbers and in many different designs. These inhalers are used principally for inhaling pharmaceutically active substances or mixtures of substances, especially powdered substances or mixtures of substances. Such an inhaler is known, for example, from CH-A-666,823. The inhaler described therein comprises a storage chamber for the solids as well as an air channel which connects an air inlet opening for the air drawn in with an outlet for the solids/air mixture produced in the inhaler. For fixing the amount of solids and for introducing that fixed amount of solids into the air stream there is a metering rod which is provided with a metering recess and which is constructed to be rotatable about its longitudinal axis. In a first position, the metering recess of the metering rod picks up the amount of solids fixed by the volume of the metering recess. Then the metering rod is rotated through 180° about its axis into a second position in which the solids are able to fall out of the metering recess and thus pass into the air channel, where they are mixed with the stream of air.

the inhaler described has various disadvantages. For example, the solids must be readily flowable in order to ensure that the metering recess is always filled quickly, reliably and completely. However, since granules and other relatively coarse solids are unsuitable for inhalation, the pharmaceutically active substances or mixtures of substances, for example anti-asthmatically active substances or mixtures of substances, are frequently in the form of a very small-grained powder. However, these small-grained powders generally have the very disadvantageous property of not being flowable or of being only very poorly flowable. This in turn may result in incomplete filling of the metering recess and thus in variations in the metered amount of solids. A user who is having difficulty in breathing (for example as a result of an asthma attack) must, however, be able to inhale a specific amount of powder quickly and reliably in order to obtain rapid relief.

A further disadvantage of the described inhaler is that the solids are introduced into the air channel by means of a rotatable metering rod. Solids may therefore get into the hollow spaces (bearing) around the rotatable metering rod, with the result that the metering rod can be rotated only with very great difficulty or even "siezes up" completely, which can have serious consequences especially for users prone to asthma, since the device may not be in good working order in an emergency.

A further disadvantage of the described inhaler is the fact that the small-grained powders in the storage chamber cannot be stored in a separate storage container, for example a capsule. This is especially disadvantageous for powders whose pharmaceutical activity decreases when they are stored in permanent contact with the air. Moreover, with the above-described inhaler, moisture entering the inhaler and its storage chamber (for example as a result of the user accidentally coughing into the inhaler) may cause further impairment of the flow properties of the powder, which in most cases are already poor, or may cause lumps to form.

SUMMARY OF THE INVENTION

The problem underlying the invention is, therefore, to devise an inhaler for solids which avoids the above-mentioned disadvantages, which allows rapid, simple and reliable metering of the solids, which permits storage of the solids in a separate storage container, for example a capsule, and which is simple to use. In addition, the inhaler is to be designed for a large number of inhalations, that is to say it is not to be so-called disposable inhaler.

This problem is solved by an inhaler for introducing a metered amount of solids into a stream of air drawn by a user comprising the features of the present invention. The metering rod extends through an opening in the storage chamber into that chamber. The storage chamber and the metering rod are movable relative to each other in such a manner that the recess in the metering rod is located in the storage chamber in a first relative position and in the air channel in a second relative position. The metering rod therefore dips into the supply of solids in the first relative position. With regard to the solid, a powder that is not flowable or is only poorly flowable will be considered by way of example in the following, which powder, during filling of the metering recess in the first relative position, is pressed into that recess. In addition, the powder may be stored in a separate storage container in the storage chamber, for example in a capsule. As has already been discussed, this may be of importance for powders whose pharmaceutical activity decreases when they are stored in permanent contact with the air. Moreover, storing of the powder in a capsule also protects it from any moisture which may enter, thus avoiding the formation of lumps and hence further impairment of the flow properties of the powder, as well as impairment of its pharmaceutical activity as a result of contact with the moisture.

In one embodiment of the inhaler according to the invention, the metering rod is fixed relative to the device body of the inhaler and the storage chamber is movable towards the metering rod. This embodiment is distinguished by being of simple construction and being simple to operate, as will be explained more precisely below by means of the detailed description.

Another form of the inhaler according to the invention comprises a separate operating member for moving the storage chamber. When operated, the operating member moves the storage chamber against the force of a return spring into the first position relative to the metering rod. The wall of the storage chamber is provided with a wall extension which closes the air channel in that first relative position. An opening is provided in the wall extension which opens the air channel again once the storage chamber has been returned to the second relative position. Owing to this design of the inhaler, it is not possible either to inhale or to blow (for example cough) into the air channel while the metering recess is being filled, as a result of which moisture is prevented from entering the air channel when the metering rod and the storage chamber are in that position relative to each other. When the amount of powder has been removed from the storage chamber, or from the storage container located therein, the storage chamber is returned to the second relative position and the filled metering recess of the metering rod thus passes into the air channel. The opening in the wall extension of the storage chamber opens the air channel and inhalation can be carried out.

In another form of the inhaler according to the invention, the operating member is additionally provided with a shaking element which may be in the form of, for example, a snap spring. The shaking element causes the storage chamber to be shaken when the first relative position of the metering rod and the storage chamber is reached, that is to say when the metering recess is being filled, with the result that the metering recess is filled completely, reliably and quickly even in the case of especially poorly flowable powders.

In order to indicate to the user that he has just carried out a metering operation, and also to allow shaking of the storage chamber in the case of poorly flowable powders while the metering rod with the metering recess is extending into the powder, a development of the inhaler according to the invention is provided with a locking device. This locking device holds the storage chamber and the metering rod in the first position relative to each other. When metering is complete, the lock can be released again by operation of an unlocking element. Unintentional multiple metering operations are also avoided in this manner.

In an advantageous form of the invention, the inhaler has a separate suction piece in which the cross-section of the air channel widens towards the outlet. Such a suction piece works in the opposite way to a nozzle and effects complete dispersion of the powder so that the powder can pass in the air stream into the user's lungs. A closing cap in which a drying agent is provided may be placed on the suction piece in order to remove any moisture which may have entered.

In order to prevent the user, once the amount of powder has been fixed and the powder has been introduced into the air channel, from blowing the powder out through the air inlet by blowing (for example coughing) into the inhaler, another form of the invention provides a non-return valve at the air inlet.

Another form of the inhaler according to the invention is provided with a resettable counter which is incremented when the first relative position of the storage chamber and the metering rod is reached. The user can therefore see how many metering operations he has already carried out, or how many metering operations remain, and can refill the storage chamber if necessary.

The inhaler is especially suitable for the inhalation of substances or mixtures of substances having anti-asthmatic activity, for example for a mixture of formoterol and lactose, as will be explained in more detail below.

In a very important embodiment of the invention, the axial displacement of the metering rod is effected by the rotation relative to each other of the device body or housing part carrying the rod on the one hand and the housing part containing the storage chamber on the other, that rotary movement being forcibly converted into an axial movement by means of sloping surfaces. Accordingly, in the inhaler according to the invention, a housing part containing the storage chamber and the device body carrying the metering rod are displaceable relative to each other from a first position, in which they are pushed together, into a second position, in which they have been moved apart, by virtue of their being rotatable relative to each other and of at least one sloping surface on the device body and/or the housing part and a counter-member guided on that sloping surface converting the rotary movement into an axial movement. This results in a considerably more convenient metering movement, because a rotary movement can be carried out more reliably than can a relatively short axial movement in which two parts have to be moved apart.

The housing part or device body may have several sloping surfaces of the same gradient and length distributed over its periphery, and the body or part that is rotatable relative to that first housing part or device body may have the corresponding number of projections or counter-members cooperating with those sloping surfaces. The rotary movement is therefore converted into the axial movement at several points simultaneously, so that the application of force is symmetrical and the axial displacement is precise during the rotation.

It has proved advantageous for four sloping surfaces to be provided which extend over almost 90 degrees, are located level with one another and ascend in the same direction, and which cooperate with counter-members in the form of projections, and for vertically oriented openings, grooves or the like for the projections to be provided at the ends of the sloping surfaces so that, after a rotation and after the projections have slid along the sloping surfaces, with the resulting axial displacement of the metering rod, the housing part having the storage chamber and the counter-member can be pushed together in the axial direction and returned to the initial position. The sloping surfaces serving as guides therefore extend over a portion of a helix but terminate in an axial opening so that, when a rotation is carried out, first the desired axial displacement is effected, with the metered material being transported from the storage chamber into the airway, while for returning the metering rod into the storage chamber it is sufficient simply to push the device body and the housing part together axially because, at the end of the rotary movement, there are no more sloping surfaces hindering such a movement.

In order to ensure on the one hand that the above-mentioned axial return movement is possible, but on the other hand that the projection, for example a cam, is constrained to move over a sloping surface even at the beginning of the rotary movement, at least one saw-tooth projection (tooth) may be arranged in the axial return grooves, the side of the tooth that falls away steeply being aligned with the effective sloping surface for the cam, and the cam may be displaceable axially over the ascending sloping side of the tooth and, in the initial position for the next metering movement, be located behind the side that falls away steeply. During the axial displacement into the initial position, therefore, the relevant projection (cam) is able to slide over the saw-tooth projection (tooth) inside the axial return groove, but is then prevented from making a corresponding movement in the opposite direction from the other side, so that the saw-tooth projection also forms part of the guide or sloping surface which contributes towards converting the rotary movement of the two housing parts relative to each other into an axial movement.

The sloping surfaces advantageously correspond to sectors of a screw thread and are arranged especially on the inside of a wall portion of the housing part. In that case, the device body is provided with the projections that cooperate with the sloping surfaces. Of course, it is also possible for the sloping surfaces to be provided on a wall portion of the device body and for the housing part to have the projections that cooperate with the sloping surfaces.

The embodiment of the inhaler in which introduction of the solids is effected by converting a rotary movement into an axial movement permits a design of considerable importance, in which on the one hand rotation of the housing parts contrary to the metering movement is prevented, and in which the rotary movement can at the same time be used to shake the inhaler in such a manner that the powdered solids are readily able to flow into the metering recess. Such an advantageous development may consist in arranging at contact points between the housing parts which are rotatable relative to each other a locking mechanism, ratchet or the like which prevents the housing parts from being rotated contrary to the direction of the metering movement. As a result, on the one hand incorrect operation is ruled out, since the user is able to rotate the device in only one direction, and on the other hand the ratchet causes the device to be shaken sufficiently during the rotation to enable the powder to flow readily into the metering recess.

The locking mechanism may comprise a ratchet wheel having saw teeth on one housing part and counter-teeth or groups of counter-teeth, which are offset relative to one another in the circumferential direction, on the other housing part or device body, the offset of the counter-teeth relative to one another in the circumferential direction being so selected that the catch intervals of the locking mechanism are smaller than the tooth pitch. In such a locking mechanism it is sufficient for one tooth of the ratchet wheel to engage with one counter-tooth. Since the inhaler is provided with several counter-teeth offset relative to one another in the circumferential direction, the offset of the counter-teeth being different from the tooth pitch, correspondingly small intervals are produced in the direction of rotation, after each of which intervals the device is again locked. The device is also shaken a corresponding number of times during the entire rotary movement.

In this connection it is advantageous for the teeth, the tooth spaces and the counter-teeth to extend in a straight line in the axial direction. They therefore do not hinder the return movement which is to be carried out at the end of the metering movement.

In order to be able to accommodate on the one hand the guide or sloping surfaces and on the other hand the ratchet or locking mechanism in a small area, the device body or housing part having the metering needle may have a double wall in places, the inner wall of that double wall carrying the projections which project radially outwards from that inner wall and which cooperate with the sloping surfaces on the other housing part, and the outer wall can enclose from the outside the wall portions, having the sloping surfaces, of the other housing part and contain the counter-teeth for the ratchet wheel arranged on the outside of the housing part containing the storage chamber. In practice, therefore, the device body has two walls into the space between which a corresponding wall of the housing part can engage, which wall can then carry on one side the sloping surfaces and on the other, outer side a part of the locking mechanism. Such a very space-saving arrangement of various cooperating components of the overall system is possible especially owing to the fact that, as a result of their rotatability relative to each other, the parts are circular and thus allow the various walls to be arranged concentrically.

While the inner wall of the housing part having the metering needle and the wall, having the guide surfaces of the housing part having the storage chamber are circular-at least in the region in which they cooperate-the outer wall of the first housing part may have a cross-section that differs from that circular shape, so that corner regions are formed between the walls, and, especially when the housing parts have been rotated and/or moved apart axially, the air can be drawn in via those corner regions, which are then open, and guided via openings in the inner wall portions, and also via at least one non-return valve, to the metering channels and the metering needle. The fact that the cross-sectional shape of the outer wall differs from a circular shape also allows the provision of counter-catch teeth on the inside of the wall, which teeth are offset relative to one another in the circumferential direction in such a manner that the ratchet wheel abuts a counter-tooth after even less than one tooth pitch.

Furthermore, on rotation, the corner regions move outside the overall outline, so that the admission of air is facilitated.

In the position in which the housing parts are pushed together, the end face of the outer wall of the housing part containing the metering needle may rest against a stop surface of the other housing part having a matching encircling shape, and in that position the airway can be cut off and the interior of the inhaler can be closed in an airtight manner. This has the advantage that no moisture can enter while the device is not in use, so that caking of the powder to be metered as a result of moisture when the device is next used is avoided.

The fact that, according to the invention, the two housing parts can be rotated relative to each other in order to carry out the axial displacement of the metering rod permits a further advantageous and expedient form of the invention, in that one housing part may contain an indicator ring which is rotatable relative to an indicator window and which can be advanced by a small angular amount of the same size and the same direction as a result of the rotation of the two housing parts relative to each other when metering is carried out. By means of the indicator ring, therefore, the user is able to see indirectly how empty the inhaler is, that is to say he can start using a new inhaler in good time or—where possible—he can refill the existing inhaler.

The indicator ring may be in the form of a toothed wheel which is mounted eccentrically with respect to an internally toothed wheel or an internal toothing in the housing part containing the metering needle and the external toothing of which fits into the internal toothing of that internally toothed wheel, the number of teeth on the inner toothed wheel differing from the number of teeth on the internally toothed wheel by such a small amount that the inner toothed wheel is rotatable relative to the internally toothed wheel by approximately a single revolution or a fraction thereof when a given number of metering operations, for example 200, has been carried out. The numerous partial rotary movements carried out with the individual metering operations therefore lead to a very slow, gradual rotation of the indicator ring, which can indicate to the user through the indicator window, by means of specific colours or the like, the reduction in the amount of solids available for inhalation. In this connection it is again advantageous for rotary movements of the device to take place in one direction only, and for backward rotations to be prevented.

In order to prevent the user from trying to inhale further once the given maximum number of individual metering operations has been carried out, it is possible for the toothed wheel acting as the indicator ring, and hence the metering movement, to be blocked once the given number of metering operations has been reached. This may be achieved by various methods.

One advantageous possible method, which at the same time makes use of the axial movement brought about by the rotation, is as follows: the toothed wheel acting as the indicator ring has a stop which cooperates with a counter-stop on the housing part rotatable relative to the toothed wheel, in such a manner that the two stops are close to or touching each other in the initial position and can gradually be moved apart in the circumferential direction as a result of the metering movements, the two stops coming to lie, as a result of the simultaneous axial displacement, in two planes which are offset vertically relative to each other, and returning to a common plane as a result of the return movement, and, after approximately one revolution of the indicator ring and a last metering operation, the two stops-which are advantageously in the form of projections-lie above each other in the two planes in such a manner that the axial return movement into the initial position, and therefore a further metering operation, is prevented.

In another form of the invention which is of considerable advantage there is arranged in the storage chamber, at the end remote from the metering rod, a piston or the like which is acted upon by a weak spring and moves with the contents of the chamber as the latter empties, the strength of the spring being sufficiently slight to prevent compression of the solids but sufficiently strong to push the piston, against the weight of the solids and against the piston's own weight, so that it moves with the solids in the chamber as the latter empties. As a result of this arrangement it is possible to use the inhaler in virtually any position and nevertheless ensure that the metering recess is filled with every metering movement. Furthermore, this measure and the continuous slight pushing of the powdered solids prevents caking of the powder or the formation of a channel at the point at which the metering rod moves in and out of the powder. The spring acting upon a following piston therefore ensures that, for each metering movement, and especially after previous shaking of the inhaler, complete metering is actually carried out.

The storage chamber may be arranged inside the housing part in such a manner that it can be removed and replaced, and/or it may have a removable cover. Consequently, when the storage chamber is empty, either the storage chamber itself may be replaced or it may be refilled, instead of a completely new inhaler having to be used and the empty one having to be discarded.

The storage chamber arranged replaceably in the housing part may have, in the initial state prior to assembly, a closure for the passageway for the metering rod, which closure can be pierced and/or is fastened in an airtight manner by means of predetermined breaking points, and which can be opened automatically by the metering rod by insertion of the storage chamber into its housing part. Therefore, when an empty storage chamber is replaced with such a new storage chamber, insertion of the new storage chamber into the housing part results in the immediate insertion of the metering rod into the storage chamber without the chamber having to be opened beforehand.

In order that the closure, which can be opened by the metering rod, cannot pass into the metering recess during subsequent use and impede the metering movements, it is advantageous for the closure of the storage chamber, which can be opened as a result of assembly, to be pivotable into the interior of the storage chamber, and for its diameter to be greater than the axial extent of the metering recess. Other technical forms of this principle are also possible.

BRIEF DESCRIPTION OF THE DRAWINGS

Embodiments of the invention are described in more detail below with reference to the drawings, some of which are diagrammatic and in which:

FIG. 10 is a section along line X—X of FIG. 11 through the locking device in the initial state (second relative position), FIG. 11 is a plan view of the locking device according to arrow XI in FIG. 10.

DETAILED DESCRIPTION OF THE INVENTION

Figure 1:
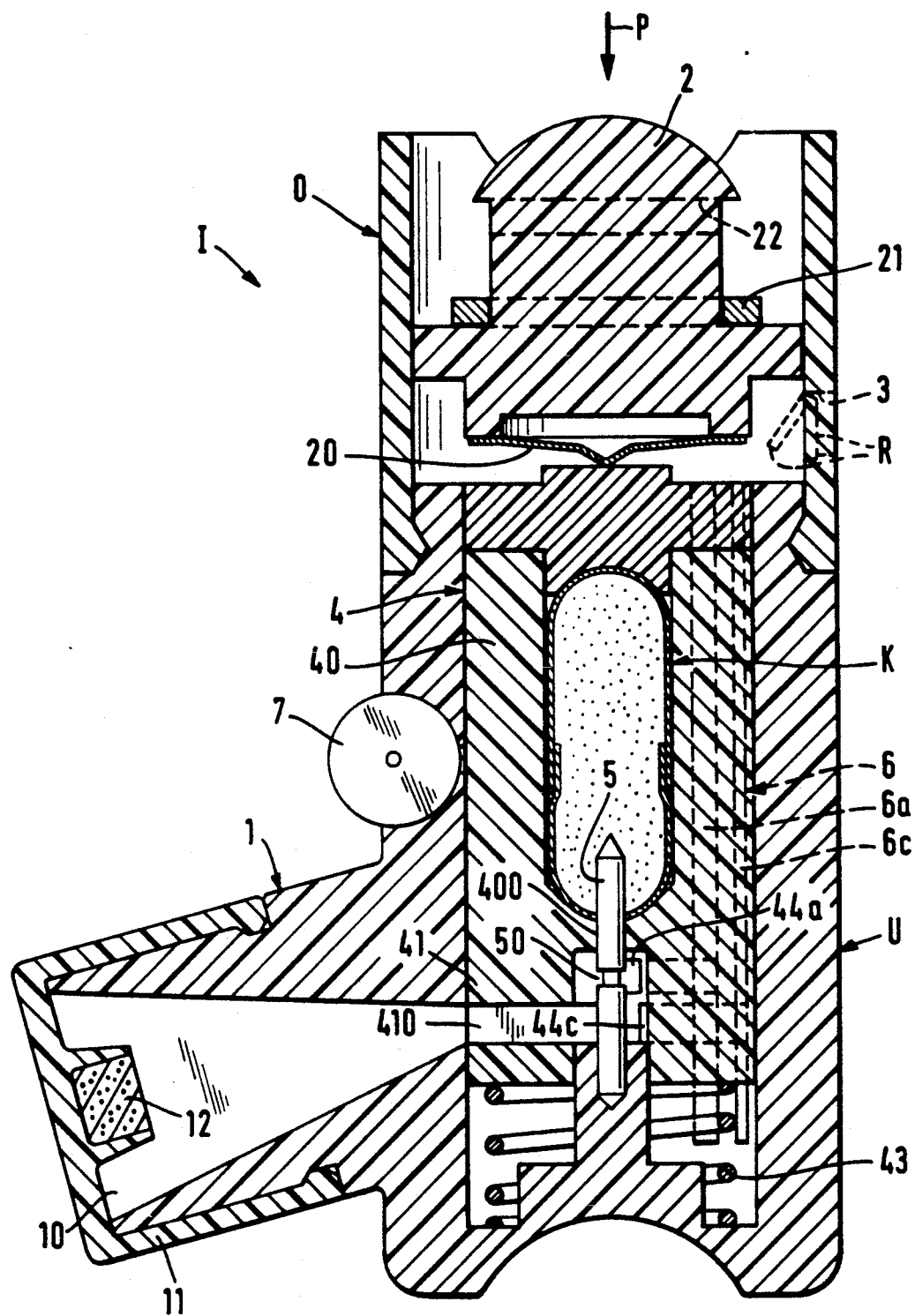
FIG. 1 is a longitudinal section of an inhaler according to the invention in the initial state (second relative position)
Figure 2:
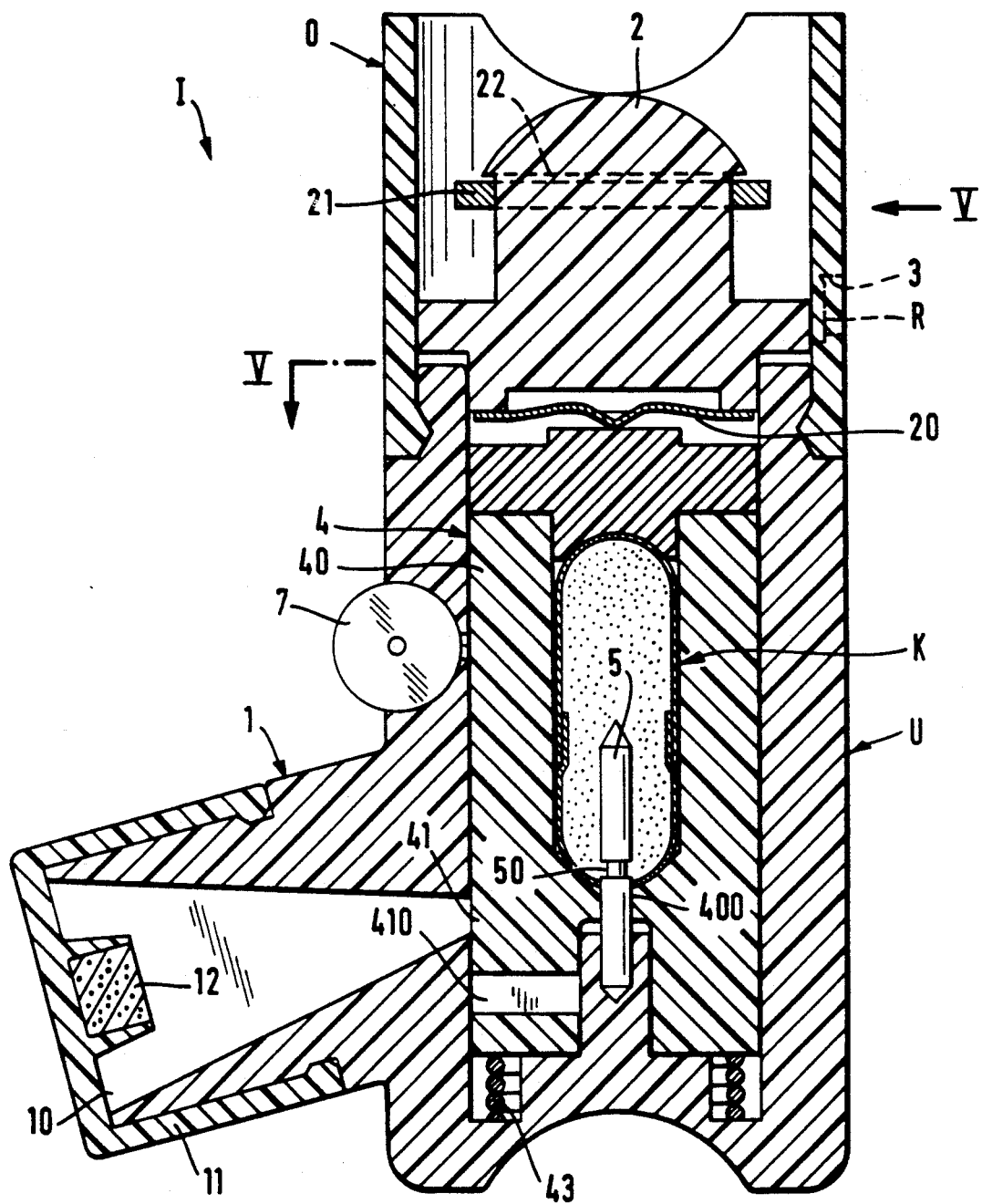
FIG. 2 is a longitudinal section through the inhaler of FIG. 1 in the first relative position.

The longitudinal sections through the inhaler shown in FIGS. 1 and 2 are intended to explain its construction and operation in more detail. The inhaler I essentially comprises an air inlet 3 with a non-return valve R shown by way of suggestion (both shown by broken lines, since they do not lie in the plane of section) in its removable upper part O, an operating member in the form of a push-button 2, a storage chamber 4 for the solids or for a separate storage container, for example a capsule K, in which the solids are stored, a metering rod 5 provided with a metering recess 50, which in the present case is in the form of a groove by way of example, an air channel 6 (shown by a broken line, since it does not lie in the plane of section), and a suction piece 1 provided with an outlet 10 for the solids/air mixture produced in the inhaler in a manner which has yet to be described. A protective cap 11 is placed on the suction piece 1, by means of which protective cap 11 the outlet 10 can be closed.

In the following description of the operation of the inhaler, it is assumed that the solids are stored in a capsule K which contains, for example, 100 doses, and that the capsule K is already inserted in the storage chamber 4. The dimensions of the capsule K and the dimensions of the storage chamber 4 are matched to each other. If the push-button 2 is now inserted and the upper part O is fitted, and if the push-button 2 is pushed into its initial position, the metering rod 5 pierces the capsule K through the opening 400 in the storage chamber 4 and extends into the solids stored in the capsule K. The inhaler is now in its initial state (FIG. 1), from which first of all metering of the solids and then inhalation may be carried out.

The storage chamber 4 with the capsule K stored therein is in the rest position in FIG. 1. In this rest position the storage chamber 4 and the metering rod 5 are so arranged relative to each other that the metering rod 5 extends into the interior of the capsule K and closes the opening 400 in the storage chamber 4, but the metering recess 50 is still located in the airway between the inlet 3 and the outlet 10. This relative position (initial state) of the metering rod 5 and the storage chamber 4 is hereinafter referred to as the second relative position. The wall 40 of the storage chamber 4 is provided with a wall extension 41 in which there is an opening 410. In this relative position of the storage chamber 4 and the metering rod 5, the opening 410 opens the airway from the air inlet 3 to the outlet 10 via the air channel 6. The lower end of the wall extension 41 of the storage chamber 4 abuts a return spring 43 which in this second relative position is relaxed, apart from the necessary prestressing of the mechanism.

In order to carry out a metering operation, the user presses the push-button 2 from above according to arrow P. In the embodiment described here, the push-button 2 is provided with a shaking element which is in the form of a snap spring 20. The snap spring 20 is fastened to the push-button 2, for example it may be adhesively bonded thereto. The operation of the snap spring 20 will be discussed in more detail later. The only important consideration for the present is that the strength of the snap spring 20 is greater than the average strength of the return spring 43. As a result of the pressure on the push-button 2 from above according to arrow P, the storage chamber is moved downwards and the return spring 43 is compressed. The snap spring 20 remains in its rest state owing to its greater spring strength. The metering rod 5, which is fixed relative to the device body (for example inserted in a bore), penetrates deeper into the solids stored in the capsule K as a result of the downward movement of the storage chamber 4. When the return spring 43 is almost completely compressed, the groove-like metering recess 50 in the metering rod 5 is already located inside the capsule K and thus in the solids.

Even while the metering recess 50 in the metering rod 5 is entering the storage chamber 4, but especially when the position is reached in which the return spring 43 is completely compressed, which is hereinafter referred to as the first relative position, the groove-like metering recess 50 in the metering rod 5 is being filled with solids. In order to ensure that the metering recess 50 is filled quickly, reliably and completely even with extremely poorly flowable and very small-grained powders, which have already been mentioned at the beginning, the snap spring 20 jumps abruptly into the state shown in FIG. 2 as a result of the increasing spring strength of the almost completely compressed return spring 43 during the final stages of its movement. This abrupt jumping of the snap spring 20 shakes the storage chamber 4 and hence the capsule K stored therein and the powder, so that even extremely poorly flowable powders pass into the metering recess 50. Alternatively, the snap spring 20 could, of course, be dispensed with and the user could shake the inhaler sharply in order to achieve the described effect.

The storage chamber 4 and the metering rod 5 are now in the first position relative to each other, which is shown in FIG. 2, and the wall extension 41 therefore closes the path for the air stream. As a result, no powder can be blown out of the inhaler through the air inlet 3 if the user blows into the suction piece 1, for example by accidentally coughing, during the metering operation. In addition, closing of the airway in this manner also means that no moisture can enter the inhaler during metering, i.e. during filling of the metering recess 50, as would otherwise be quite conceivable if the user accidentally coughed.

When the snap spring 20 has jumped into its new position, the metering recess 50 is filled with powder. If the push-button 2 is then released, the return spring 43 moves the storage chamber 4 back into the second relative position, i.e. into the initial position. In that second relative position (initial position), the opening 410 in the wall extension 41 of the storage chamber 4 opens the airway, as has already been described. If the user then draws in air through the suction piece 1, a stream of air is produced in the air channel 6 through the air inlet 3 and through the non-return valve R which is indicated symbolically by a broken line in FIG. 1 by the flap R. This stream of air blows the metered amount of powder out of the metering recess 50. In this manner there is formed the solids/air mixture, which is then inhaled by the user through the outlet 10 of the suction piece 1 and can pass into the user's respiratory tract. In order to ensure that the metered amount of powder is blown out of the metering recess 50 as effectively as possible and to reduce the speed of the stream of solids/air mixture as it enters the user's respiratory tract, in the suction piece 1 the cross-section of the air channel, which is otherwise kept small, widens towards the outlet 10.

Figure 3:
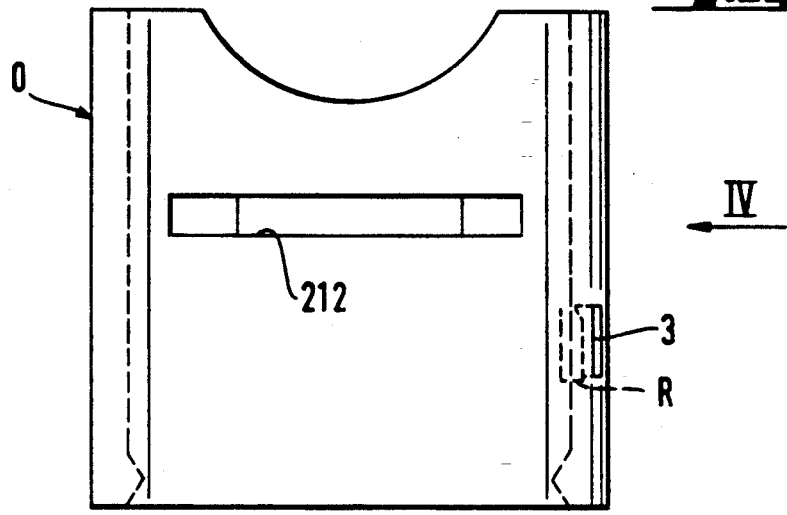
FIG. 3 is a front view of an upper part of the inhaler (into the plane of the paper of FIG. 2)
Figure 4:
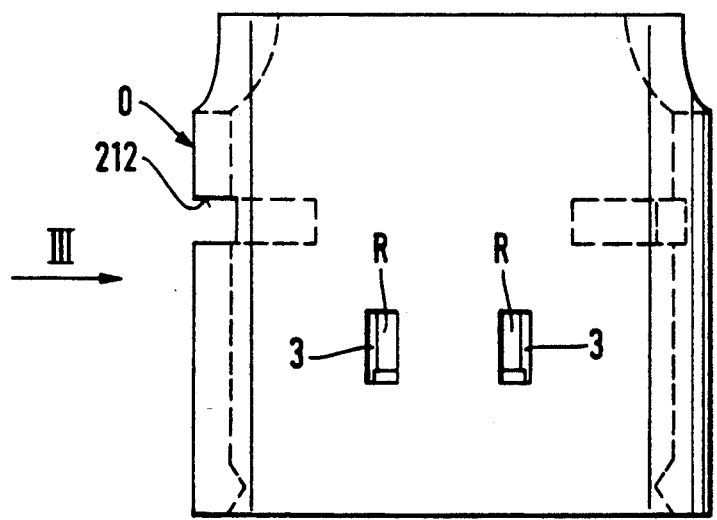
FIG. 4 is a side view of the upper part according to arrow IV of FIG. 3.

The manner in which the air channel 6 in the embodiment described here is constructed in detail, or the manner in which the air stream is guided in the inhaler, will be described more precisely below with reference to FIGS. 3 to 9. FIGS. 3 and 4 show the upper part O of the inhaler, the side view of FIG. 4 showing the air inlets 3 (elongate slots). The air drawn in passes into the interior of the inhaler through those air inlets 3 and through the non-return valve R (shown by broken lines in FIG. 1 both in its rest position and in the position it assumes during breathing in).

Figure 5:
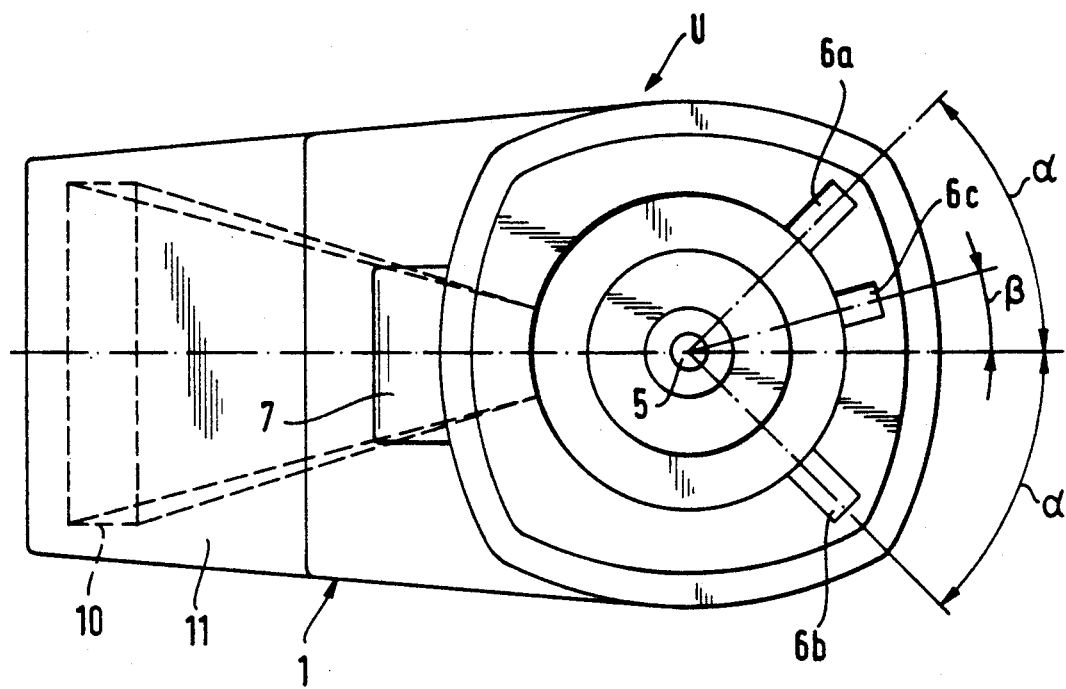
FIG. 5 is a plan view of a lower part of the inhaler according to arrow V of FIG. 2.

FIG. 5, which shows a plan view of a lower part U of the inhaler, shows how the air stream is conveyed further inside the inhaler. Three air channels 6a, 6b, 6c can be seen, which air channels are let into the body of the lower part U of the inhaler so as to lead downwards (see also the broken line 6 in FIG. 1) and through which the air stream is conveyed further.

Figure 6:
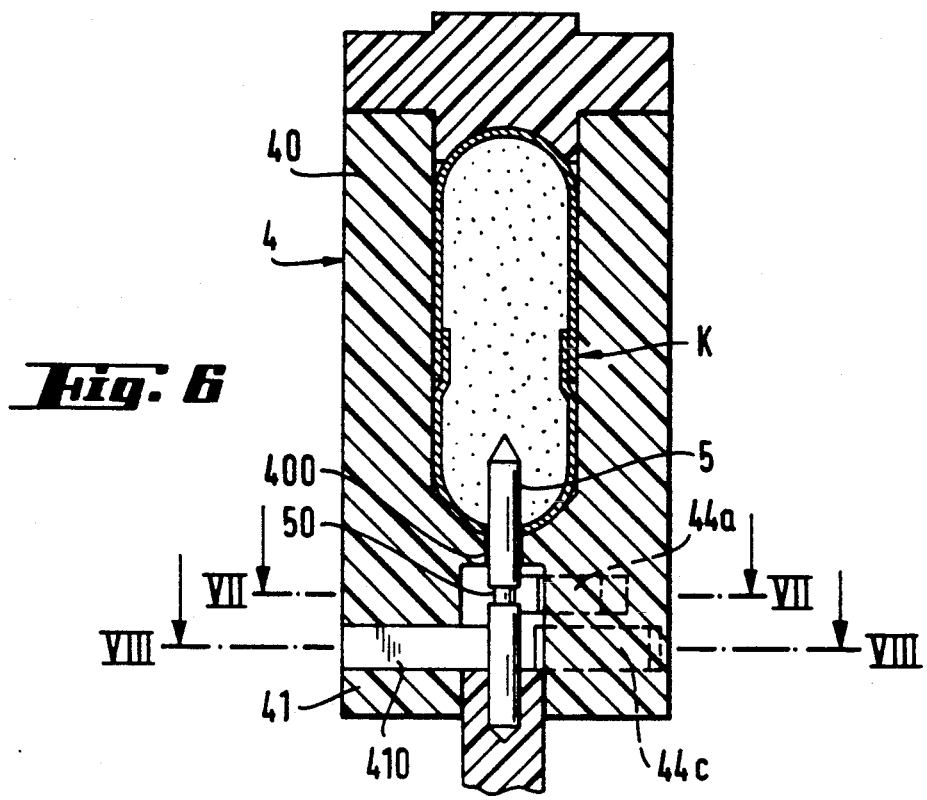
FIG. 6 is a longitudinal section through a storage chamber of the inhaler (plane of section identical with the plane of section of FIGS. 1 and 2)

FIG. 6 shows the storage chamber 4 which is movable by means of the push-button 2, but without a capsule K inserted. On completion of a metering operation, i.e. when the metering rod 5 and the storage chamber 4 are in the initial position (second relative position), the powder is blown out of the metering recess 50 in the metering rod 5 by means of air. For that purpose, however, the air stream has to pass from the air channels 6 to the metering recess 50.

Figure 7:
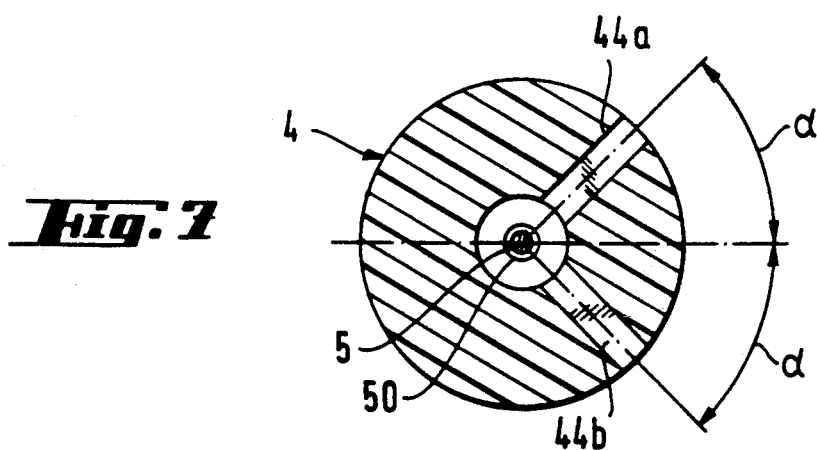
FIG. 7 is a section through the storage chamber along line VII—VII of FIG. 6.
Figure 8:
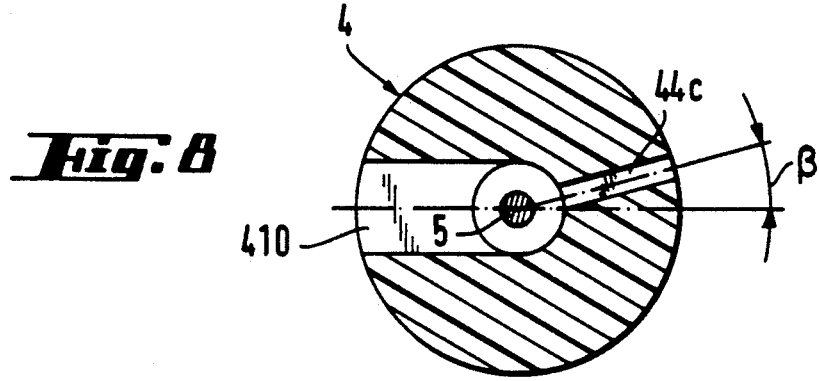
FIG. 8 is another section through the storage chamber along line VIII—VIII of FIG. 6.

The manner in which this may be achieved is shown in FIGS. 7 and 8, which show sections along lines VII—VII and VIII—VIII, respectively. The plane of section VII—VII extends precisely at the level of the metering recess, so that the latter is located in optimum manner in the air stream. It will be seen from FIG. 7 that two air inlet openings 44a and 44b for the air stream are arranged at the same angle $\alpha$ with respect to the plane of the longitudinal section of FIG. 1 as the two corresponding air channels 6a and 6b in FIG. 6.

The third air inlet opening 44c is arranged at the same angle $\beta$ with respect to that plane of section as the corresponding air channel 6c but, as shown in FIG. 8, below the other two air inlet openings 44a and 44b, in the plane of section VIII—VIII. The air inlet opening 44c serves to blow out any solids or powder grains that have fallen out of the metering recess and thus mix them with the air stream. Through the opening 410 in the wall extension 41 of the storage chamber 4, the solids/air mixture that is formed is able to pass through the outlet 10 in the suction piece 1 into the user's respiratory tract.

In order to prevent unintentional multiple metering operations, the storage chamber 4 and the metering rod 5 (see FIG. 2) are fixed relative to each other in the first relative position by means of a locking device. The locking device is indicated in FIG. 1 by way of example by a slider 21, the operation of which is described below with reference to FIGS. 9 to 13.

Figure 9:
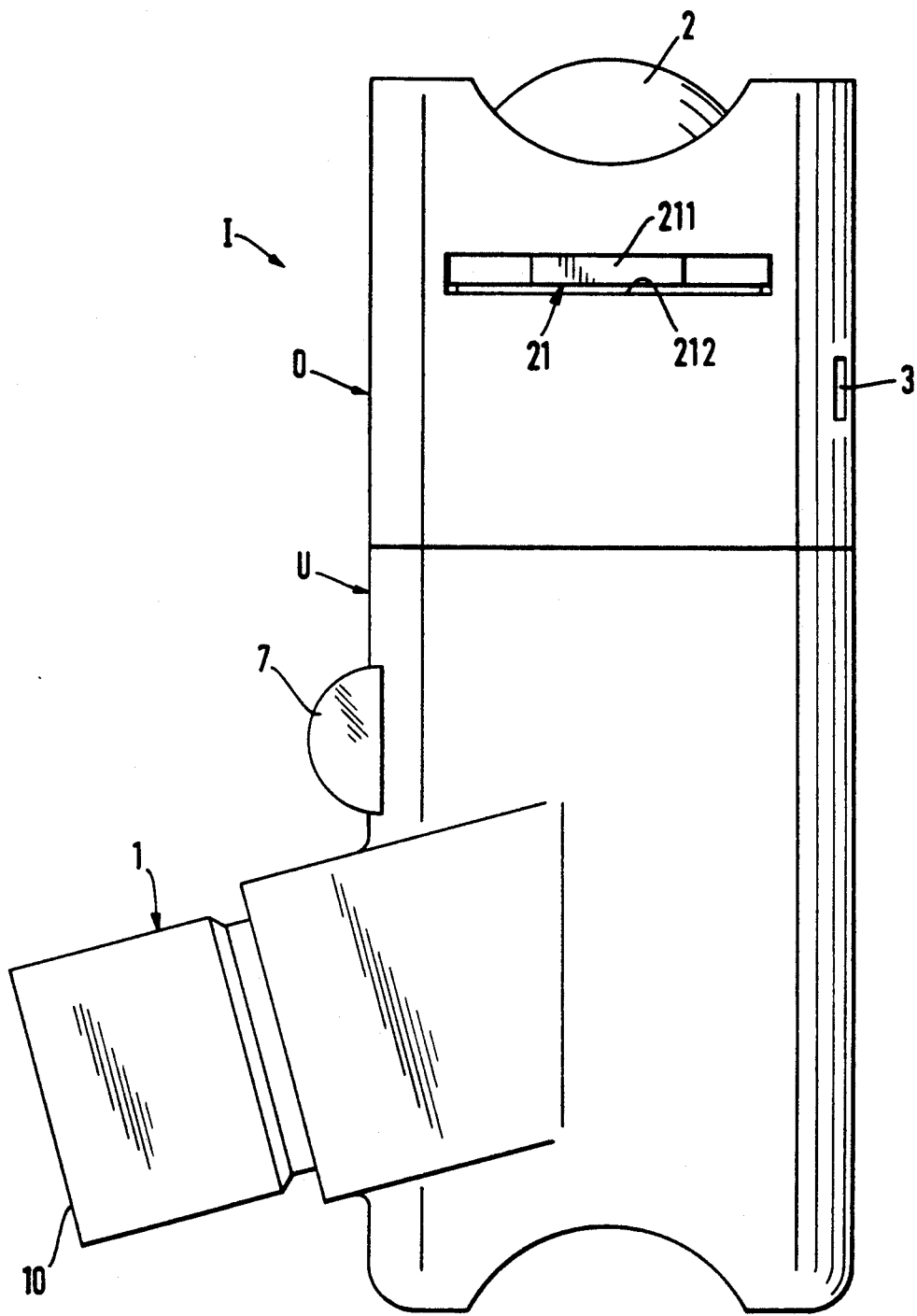
FIG. 9 shows the outer shape of the inhaler.
Figure 12:
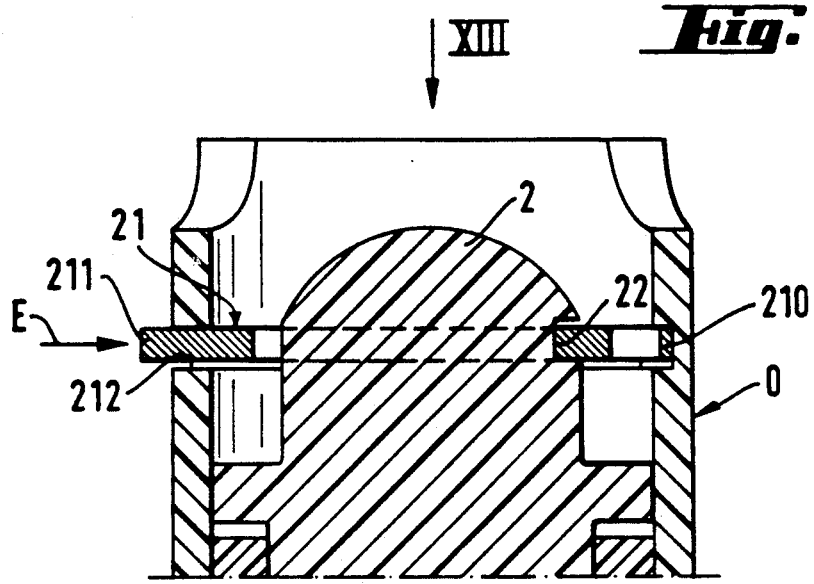
FIG. 12 is a section along line XII—XII of FIG. 13 through the locking device in the first relative position.
Figure 13:
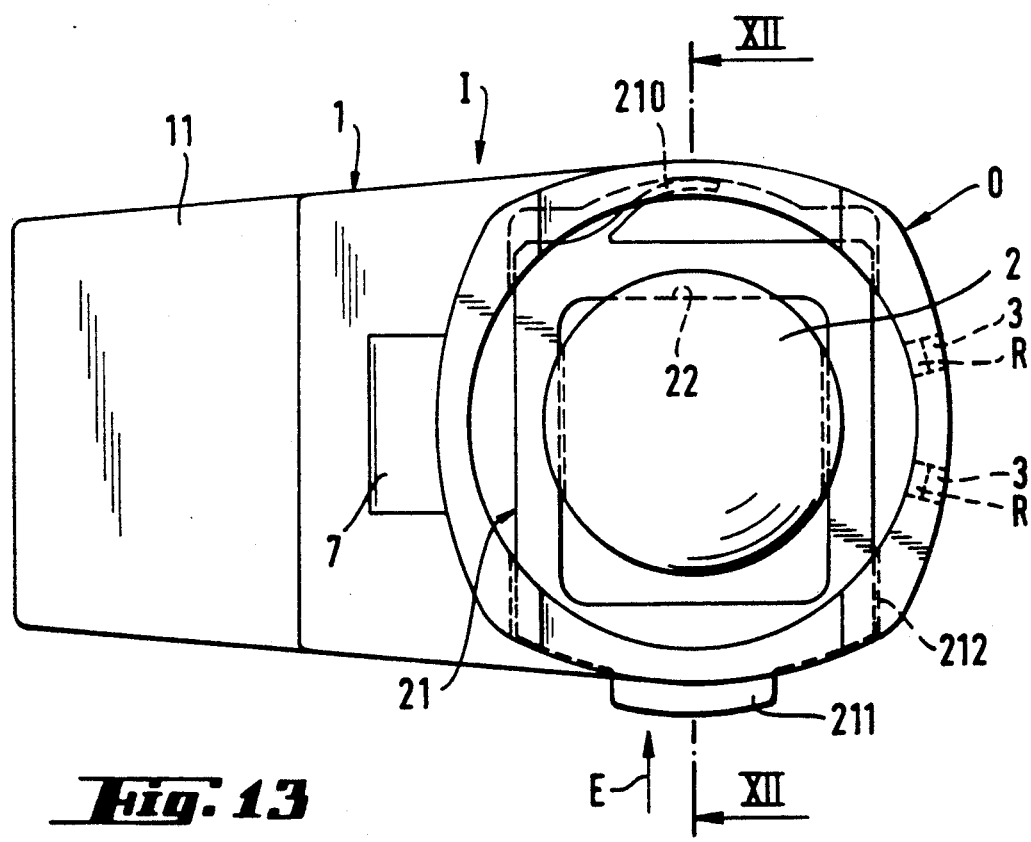
FIG. 13 is a plan view of the locking device according to arrow XIII in FIG. 12.

For the purpose of understanding the operation of the locking device, first the outer form of the inhaler is shown again in FIG. 9, an opening 212 being provided in the upper part O, as can also be seen in FIG. 3.

FIG. 10 shows a side view in longitudinal section of the push-button 2. Beneath its "head" it is provided with a groove 22, which is also shown by broken lines in FIG. 1. A slider 21, which is likewise shown in FIG. 1, is capable of engaging in that groove 22 in a manner which is yet to be explained.

FIG. 11 shows a plan view of the inhaler in its initial state (second relative position of the storage chamber 4 and the metering rod 5). This view shows that the slider 21 is provided with a leaf spring 210 and a holding button 211. The leaf spring 210 is supported against a groove in the inside wall of the inhaler (see also FIG. 10) and tries to move the slider 21 in the direction indicated by the arrow V and to push the holding button 211 even further out of the opening 212 which has already been shown in FIG. 9 and FIG. 10.

This pushing of the holding button 211 further out of the opening 212 is prevented because the slider 21 in the initial state abuts the body of the push-button 2 (operating member). This is shown especially clearly in the sectional view of FIG. 10.

If the push-button 2 is then operated (arrow P in FIG. 1), i.e. moves the metering recess 50 of the metering rod 5 into the storage chamber 4, the slider 21 initially remains in the described position since the holding button 211 is retained in the opening 212. The push-button 2, on the other hand, is moving downwards. When the first relative position is reached (FIG. 2), the slider 21 is able to slide into the groove 22 in the push-button 2 and the leaf spring 210 is therefore able to move the slider 21 in the direction indicated by the arrow V (FIG. 11). As a result, the holding button 211 is pushed even further out of the opening 212 by the leaf spring 210. In that state (FIG. 12, FIG. 13) the return spring 43 (FIG. 2) is no longer able to return the storage chamber 4 to the initial state (second relative position) because the push-button 2 is firmly engaged by way of the slider 21.

Only when the user pushes the holding button 211 from the outside in the direction indicated by the arrow E is the slider 21 moved out of the groove 22 in the push-button 2 and thus out of its engaged position and is the lock therefore released. The return spring 43 is then able to return the storage chamber to the initial state (second relative position of the metering rod 5 and the storage chamber 4). This method of locking prevents multiple metering operations from being carried out.

As has already been mentioned, the inhaler so far described may be provided with a non-return valve at the air inlet 3. Alternatively, the non-return valve R could be provided in the suction piece. The non-return valve R may be in the form of, for example, a flap, as shown by broken lines in FIG. 1, and ensures that the air inlet 3 is closed should blowing into the inhaler through the outlet 10 occur, for example should the user accidentally cough into the outlet 10. This is especially advantageous since, for example, after metering of the powder and after the storage chamber 4 has been returned to the second relative position, the powder cannot be blown out of the inhaler through the air inlet 3. Therefore, if a user accidentally coughs into the inhaler after metering, no powder is lost and the user can breathe in again without first having to carry out another metering operation.

Furthermore, the inhaler may also be equipped with a resettable counter 7 (FIG. 1) which is incremented with each metering operation. For example, the counter 7 is incremented with the downward movement of the storage chamber 4. Such a counter 7 is especially advantageous since the capsule K located in the storage chamber 4 contains a specific number of doses of the powder. When a new capsule K is inserted, the user can reset the counter 7 so that he is able to see at any time how many doses he has already taken from the capsule K and can therefore insert a new capsule K into the storage chamber 4 in good time, or, if necessary, replace the inhaler.

In order to dry, or keep dry, the interior of the inhaler or the airway, a drying agent 12, for example in the form of silica gel, is provided in the protective cap 11.

As has already been mentioned, such an inhaler is especially suitable for solid substances or mixtures of solid substances having anti-asthmatic activity, especially for the inhalation of a mixture of lactose and formoterol, which may be, for example, in the form of its salt formoterol fumarate whose name according to IUPAC nomenclature is "($\pm$)-2'-hydroxy-5'-[(RS)-1-hydroxy-2-[[(RS)-p-methoxy-$\alpha$-methylphenethyl]-amino]-ethyl]-formanilide fumarate dihydrate".

There are many possible variants of the described inhaler. In principle, it is not necessary according to the inventive concept for the storage chamber to be movable and the metering rod to be stationary; the opposite could equally apply. It is necessary merely to ensure that the storage chamber and the metering rod having the metering recess are movable relative to each other. Furthermore, it is also possible for the powder, i.e. the solids, to be stored directly in the storage chamber and not in a separate capsule which is inserted into the storage chamber. The shaking element (snap spring) may of course be of a different design, as may the locking mechanism. The drying agent may likewise be something other than the silica gel which has been mentioned.

Figure 14:
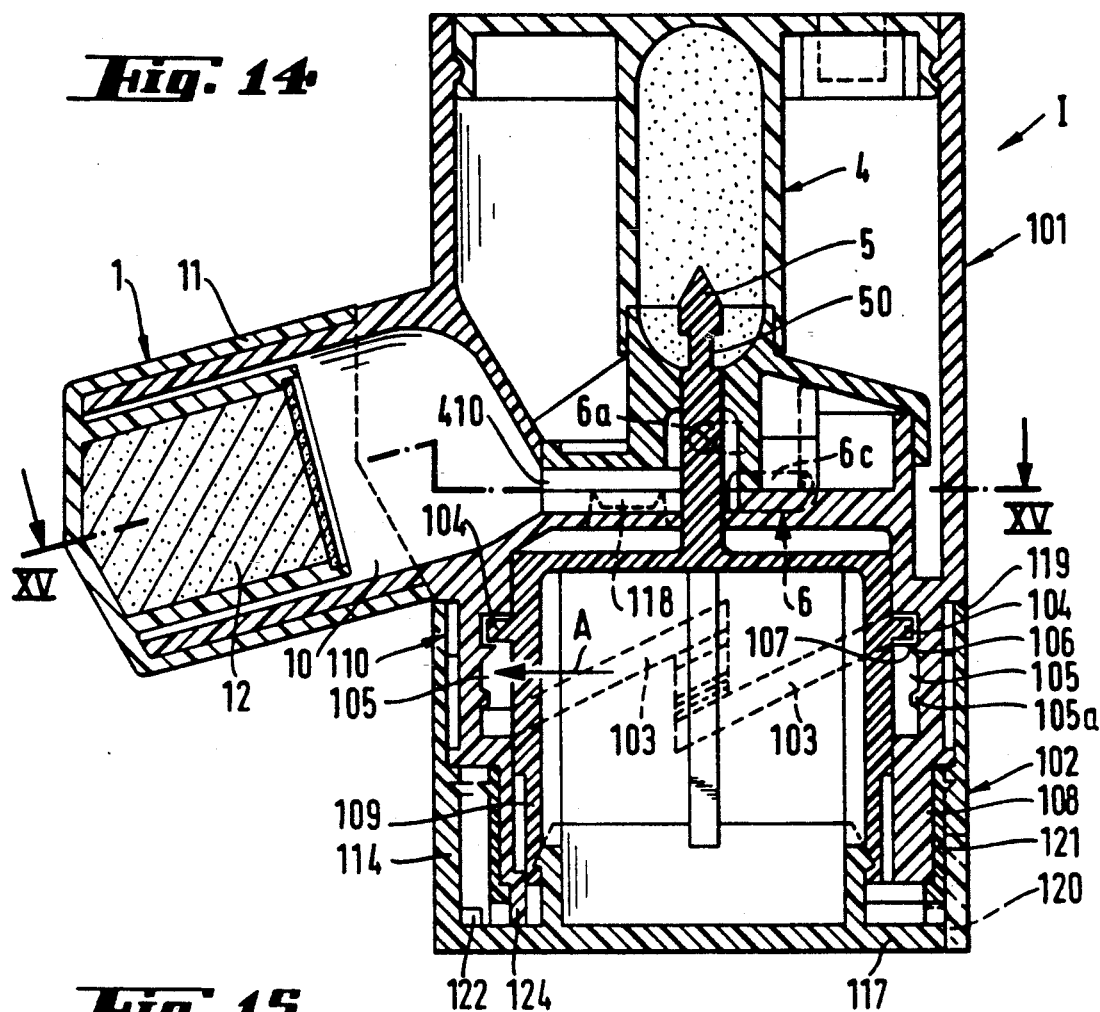
FIG. 14 is a longitudinal section through a modified inhaler according to the invention in the first relative position, in which the metering recess is positioned in the storage chamber, wherein the axial displacement can be carried out via rotation of the device body carrying the metering rod relative to the housing part containing the storage chamber.
Figure 15:
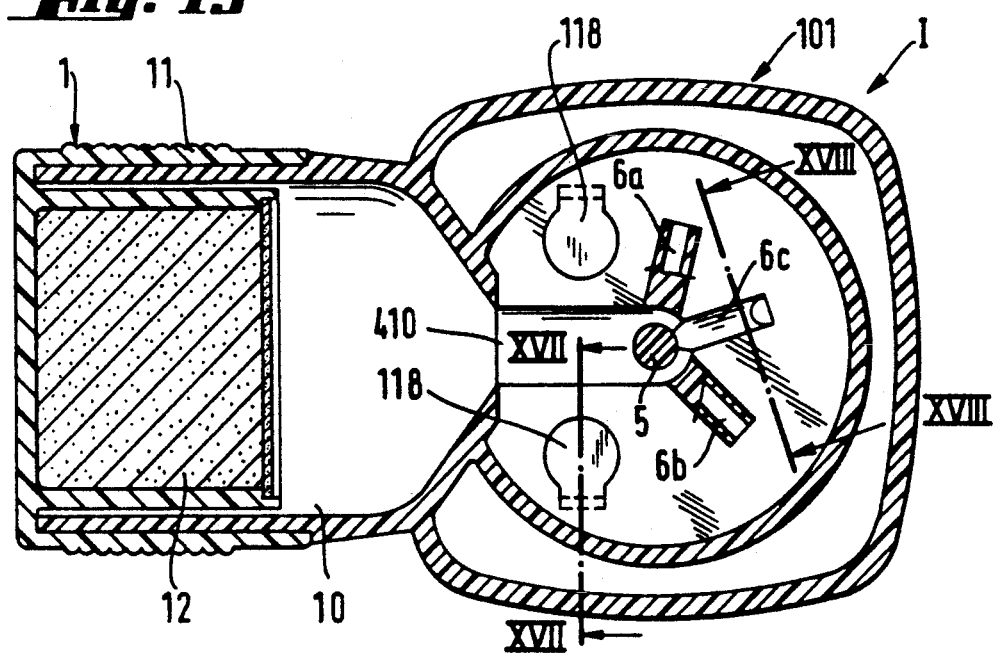
FIG. 15 is a partially diagrammatic cross-section of the inhaler along line XV—XV in FIG. 14.

FIGS. 14 to 30 show embodiments of the inhaler I in which, especially, the above-mentioned relative movement between the storage chamber 4 and the metering rod 5 is achieved in a particularly advantageous manner. The parts of this modified inhaler I have to a considerable extent been given the same reference numerals as those used in the embodiment described above. In this connection, a comparison of, for example, FIG. 1 and FIG. 14 shows that in the embodiment described below, the inhaler is likewise divided into two housing parts, but the division is below the air outlet or mouthpiece 10.

Figure 16:
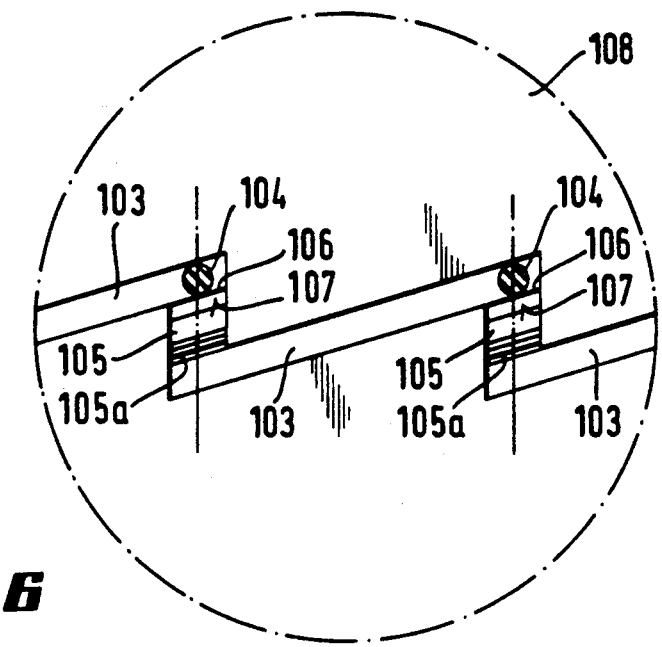
FIG. 16 is a developed view of a sloping surface on the housing part, extends over, for example, approximately a quarter circumference and by means of which, with the aid of a projection on the device body, the rotary movement is converted into the required axial displacement of the metering rod from its initial position shown in FIG. 14 into the position shown in FIG. 19.
Figure 17:
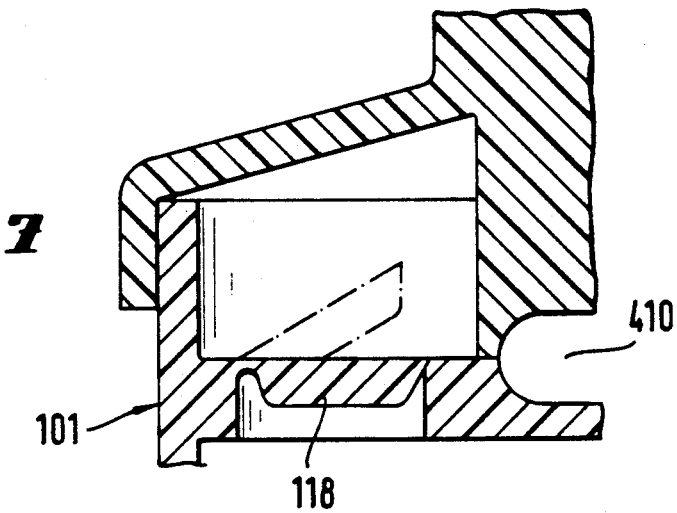
FIG. 17 is a section along line XVII—XVII in FIG. 15 through a non-return valve located inside the airway.
Figure 18:
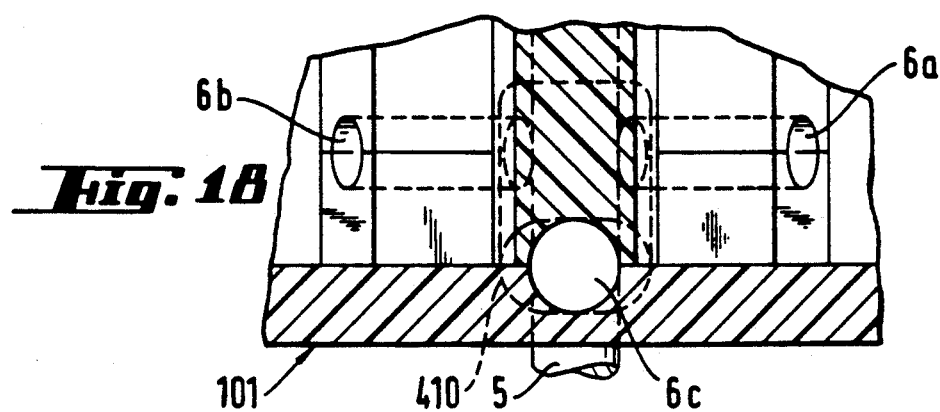
FIG. 18 is a partial section along line XVIII—XVIII in FIG. 15 through a channel leading to the metering rod, with a view of the inlets into two other channels.

In order to carry out the relative movement between the storage chamber 4 and the metering rod 5, in the embodiments described below a housing part 101 having the storage chamber 4 and the device body or housing part 102 carrying the metering rod 5 are displaceable relative to each other from a first position, in which they are pushed together, for example according to FIG. 14, into a second position, in which they have been moved apart, for example according to FIG. 19, by virtue of their being rotatable relative to each other and of sloping guide surfaces or sloping surfaces 103 on the housing part 101 and counter-members 104 provided on the device body 102 and guided on the sloping surfaces 103 converting the mentioned rotary movement into an axial movement. It should again be mentioned at this point that it is also possible for the sloping surfaces 103 to be provided on the outside of the wall 109, i.e. on the device body 102, and accordingly for the counter-members 104 to be provided on the housing part 101. A sloping surface 103 is shown in FIG. 16 as a development of view A of FIG. 14.

The housing part 101 in the embodiment has several, namely four, sloping surfaces 103 of the same gradient and length distributed over its periphery, and the housing part 102, which is rotatable relative to the housing part 101, has the corresponding number of projections or counter-members 104 cooperating with the sloping surfaces 103.

The four sloping surfaces 103, which are advantageously in the form of grooves in order to be able to guide the projection-like counter-members 104 well under proper control, extend over almost 90 degrees of the periphery, are located level with one another and ascend in the same direction. At the end of each sloping surface 103 there is provided a through groove 105 for the projection-like counter-members 104, the through grooves 105 being oriented vertically, i.e. parallel to the longitudinal centre axis of the inhaler I, so that, after a rotation and after the counter-members 104 or projections have slid along the sloping surfaces 103, with the resulting axial displacement of the metering rod 5, the housing part 101 having the storage chamber 4 and the counter-member 104 which acts as the guide rod can be pushed together again in the axial direction, i.e. can be returned to the initial position according to FIG. 14. The next rotary metering movement can then be carried out from that initial position in the same direction of rotation as the previous rotary movement. This therefore results in very simple operation for the user, the user advantageously being able to make a rotary movement which is relatively simple and reliable to perform and which is also easier for an elderly person or a child than having to carry out a relatively short axial displacement against the initial frictional resistance.

In the axial return grooves 105 there is arranged according to FIGS. 14, 16, 19, 22 and 29 at least one saw-tooth projection 106, the side of the saw-tooth projection 106 that falls away steeply being aligned with the respective effective sloping surface 103 for the counter-member or projection 104. The counter-member 104 is displaceable axially over the ascending outer sloping side 107 of the projection 106 so that, in the initial position for the next metering movement, it is located behind the side of the projection 106 that falls away steeply and is transferred during the rotary movement from that steeply falling side to the sloping surface 103. It is therefore ensured that the user can and must always carry out metering by means of a rotary movement and not, for example, by means of an axial movement by displacing the counter-members 104 along the groove 105. Furthermore, there is also provided in the axial return groove 105 a small projection or cam 105a which prevents the inhaler from being pushed together without force and perhaps unintentionally.

The sloping surfaces 103, or the grooves containing them, each correspond to a sector of a screw thread and are arranged in the embodiment on the inside of a wall portion 108 of the housing part 101, which wall portion 108 extends from the housing part 101 approximately axially to the side remote from the storage chamber 4-downwards in the Figures shown. On a corresponding wall 109 of the housing body 102, which wall 109 is parallel to the wall 108 and is arranged in the embodiment inside the wall portion 108, the counter-members 104 project radially outwards and engage in the groove-like sloping surfaces 103.

In order to replace the snap spring 20 of the embodiment according to FIGS. 1 to 13 and nevertheless produce jolts during the metering movement to shake the solids, and at the same time to exclude in an advantageous manner a rotary movement in the opposite direction to the metering movement, a locking mechanism 110 acting as a ratchet is arranged at contact points between the housing parts 101 and 102 which are rotatable relative to each other. This can be seen especially in FIG. 20, in which the return grooves 105 for the counter-members 104 can also be seen.

Figure 19:
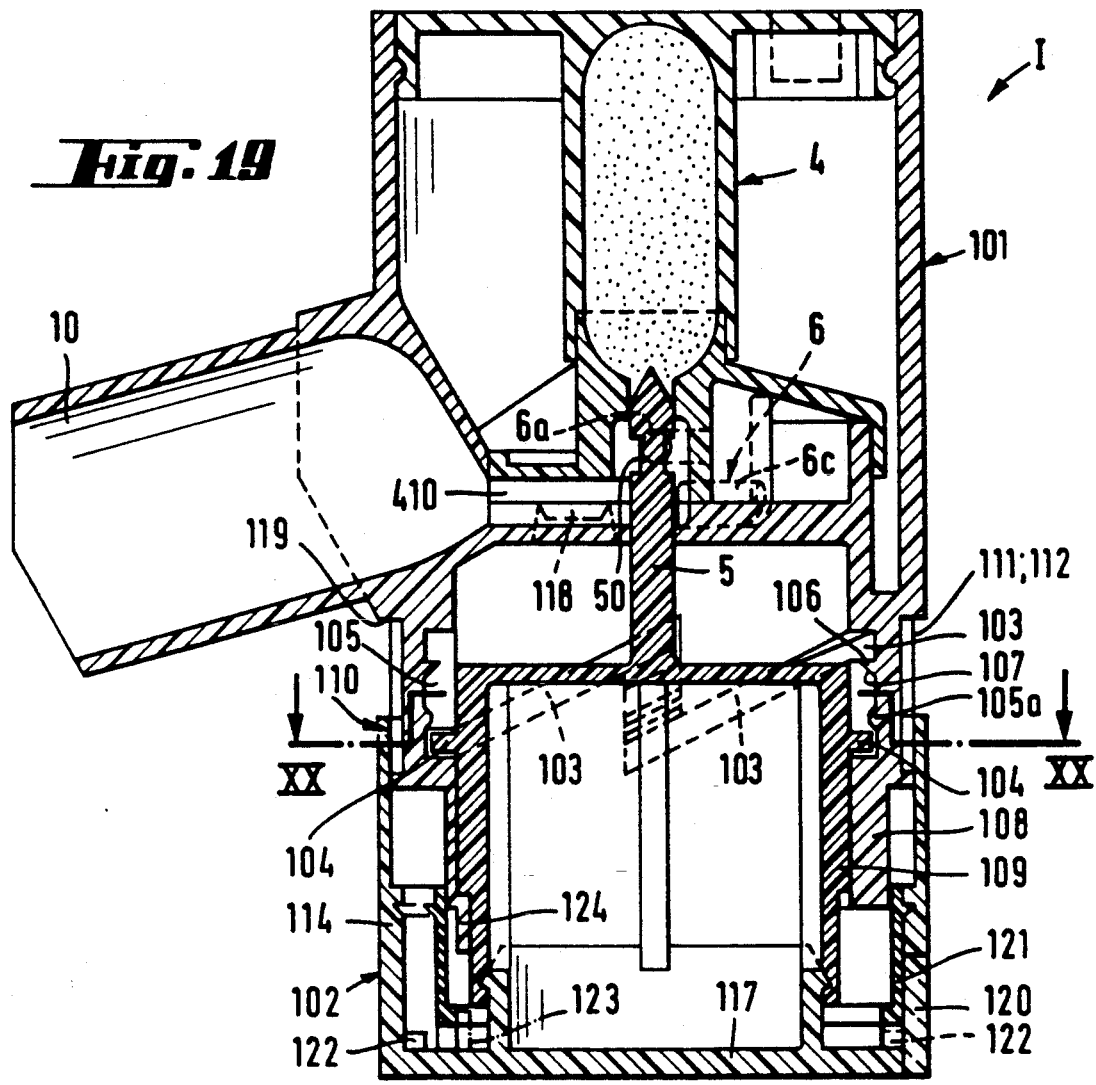
FIG. 19 is a longitudinal section of the inhaler according to FIG. 14 after execution of a rotary movement converted into axial displacement.
Figure 20:
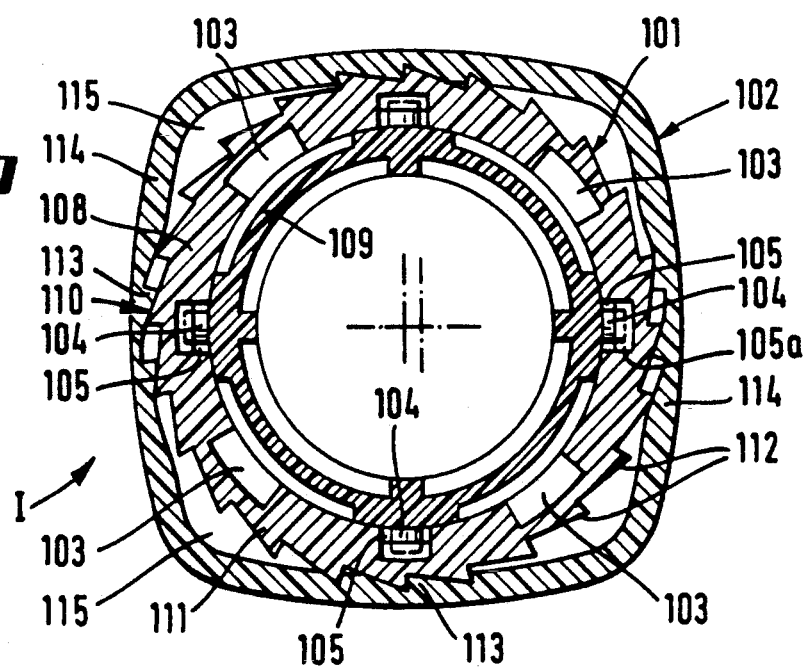
FIG. 20 is a cross-section along line XX—XX in FIG. 19 through a locking mechanism provided between the housing parts which are rotatable relative to each other.
Figure 21:
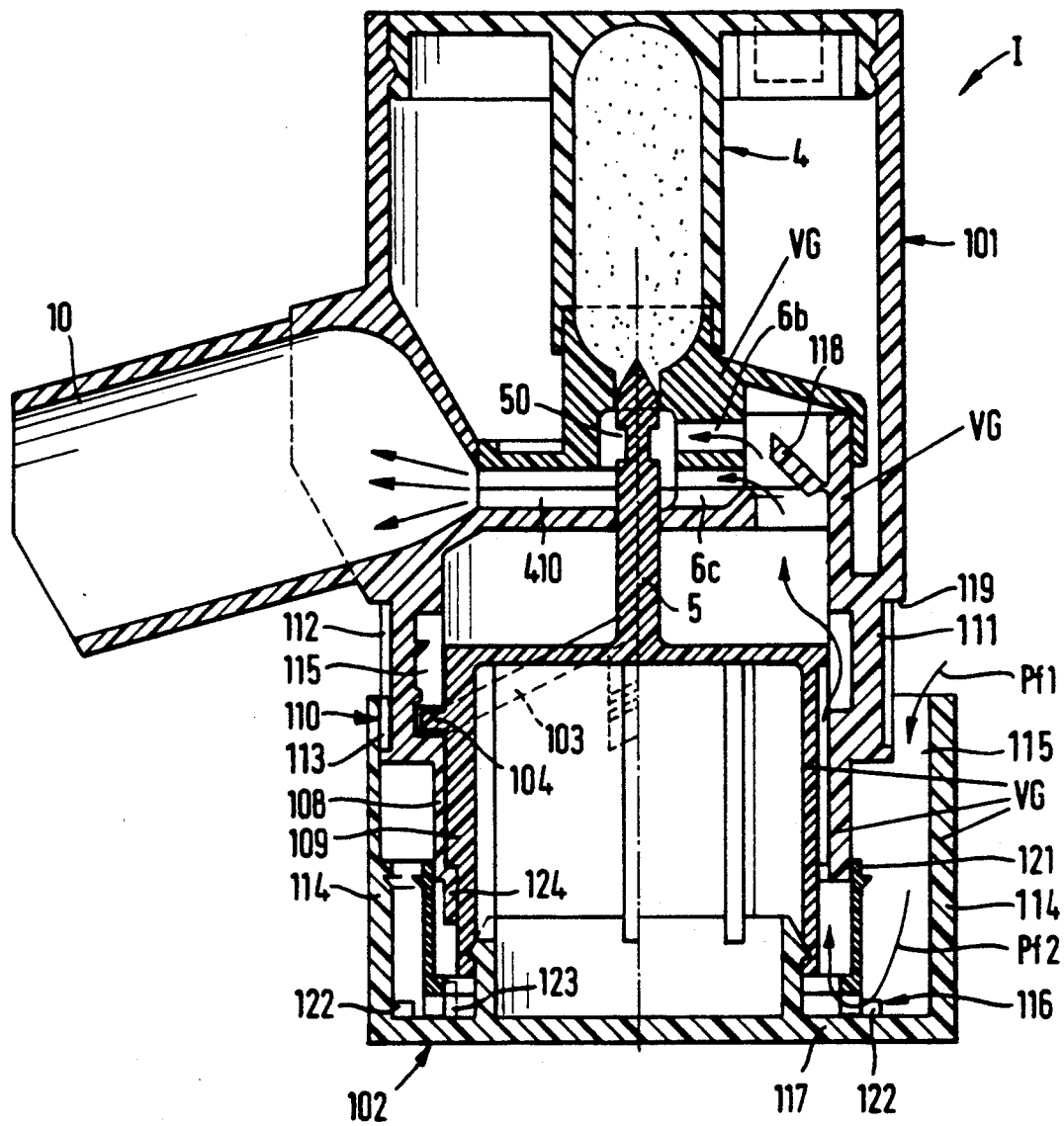
FIG. 21 is a longitudinal section of the inhaler, corresponding to FIG. 19, the righthand part being shown rotated relative to the arrangement of FIGS. 14 to 19, so that the section in this case is through the non-return valve and the air channels.
Figure 22:
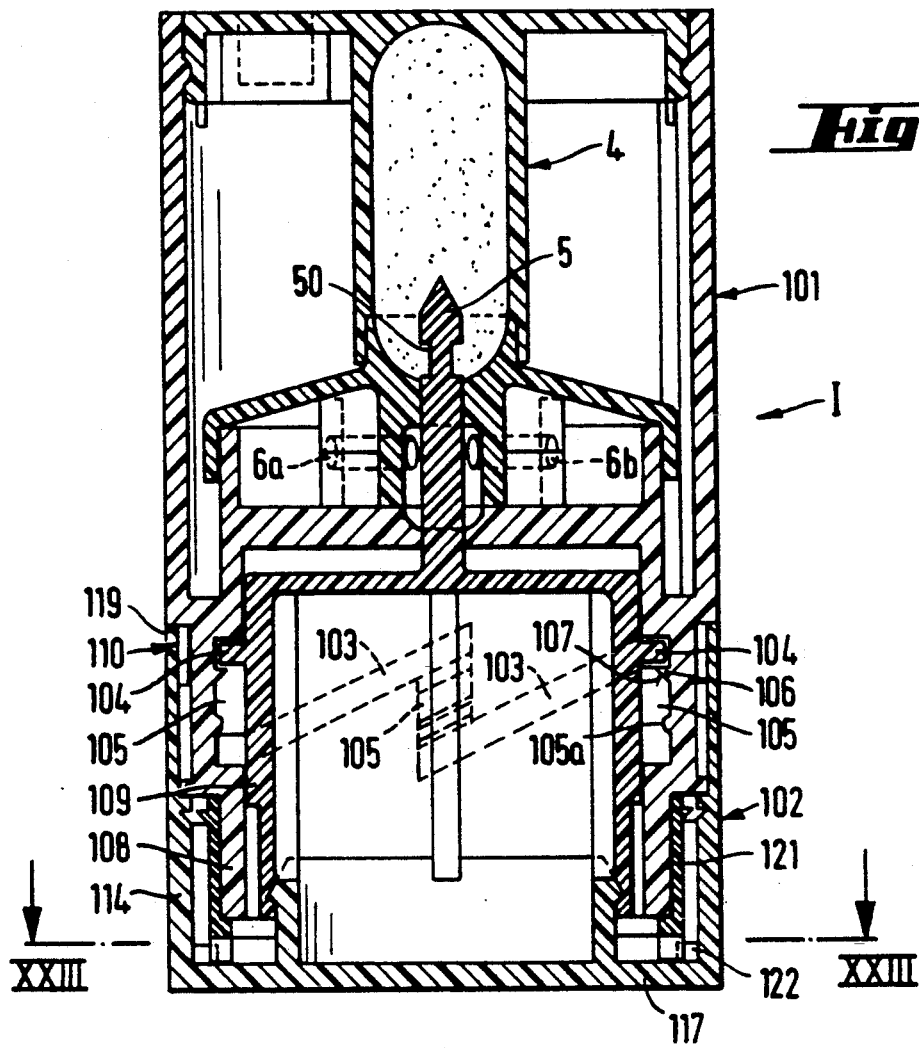
FIG. 22 is a longitudinal section of the inhaler in the first relative position, rotated through 90 degrees relative to FIG. 14.
Figure 23:
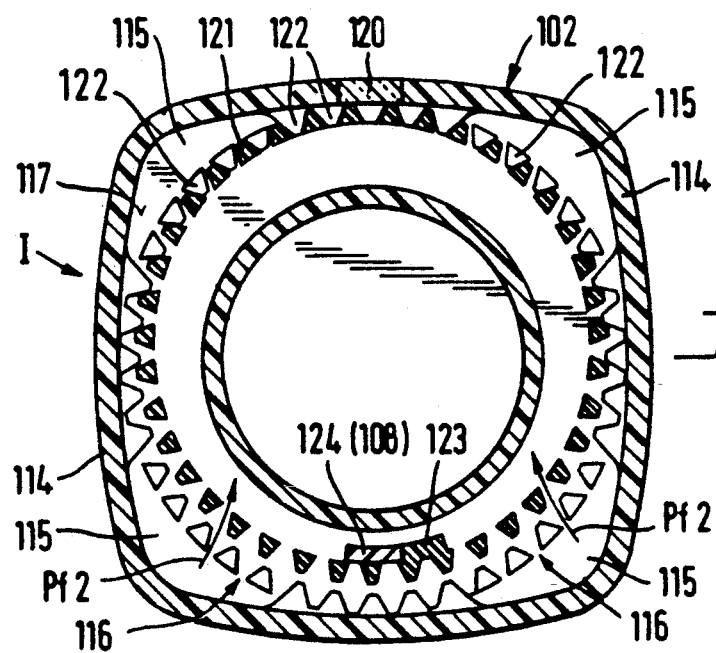
FIG. 23 is a cross-section along line XXIII—XXIII in FIG. 22 through an indicator device.

In addition, because FIG. 20 is a horizontal section along the cutting line XX—XX of FIG. 19, the sloping surfaces 103 are shown partially cut away and therefore in the form of segments in FIG. 20.

The locking mechanism 110 comprises in a manner customary per se a ratchet wheel 111 having saw teeth 112 on the housing part 101, namely on the wall portion 108, and cooperates with counter-teeth 113, or groups of such counter-teeth 113, which are offset relative to one another in the circumferential direction and are provided on the other housing part or device body 102 on the inside of an outer wall 114 which, according to FIG. 20, does not have a circular outline but, in view of the circular shape of the ratchet wheel 111, leaves corner spaces 115 free, so that the mentioned groups of counter-teeth can be offset relative to one another in the manner mentioned, so that rotation of the ratchet wheel 111 by even less than one tooth pitch again results in the opposite direction of rotation being blocked. The mentioned corner spaces 115 are also discussed below in connection with the air supply.

Especially when FIGS. 20 and 19 are considered together, it will be seen that the ratchet wheel 111 is basically a part of the wall 108 of the housing part 101 having the saw teeth 112 which project outwards and engage with the counter-teeth 113 of the outer wall 114 over a short axial region; the counter-teeth 113 have a greater axial length in order to take account of the axial relative movement between the housing part 101 and the device body 102. The teeth 112, the tooth spaces and the counter-teeth 113 extend in a straight line in the axial direction, in order to allow and also to guide the mentioned axial relative movement into which the rotary movement is of course converted.

The device body 102 or housing part having the metering rod 5 therefore has a double wall in places, the inner wall 109 of which carries the counter-members 104 which project radially outwards and cooperate with the sloping surfaces 103 on the other housing part 101, while the outside wall or outer wall 114 encloses from the outside the wall portion 108, having the sloping surfaces 103, of the other housing part 101 and contains the counter-teeth 113 for the ratchet wheel 111 arranged on the outside of the housing part 101 containing the storage chamber 4, or of the wall 108. This results in the compact construction and connection of the housing part 101 with the device body 102 shown in FIGS. 14, 19, 21, 22 and 29, even though those two parts are displaceable relative to each other not only in the axial direction but also in the rotary direction.

In order that the mentioned rotary movement may be carried out unimpeded, the inner wall 109 of the housing part 102 having the metering needle 5, and the wall 108, having the sloping guide surfaces 103, of the housing part 101 having the storage chamber 4, are of circular cross-section, while the outer wall 114 of the first housing part 102—as has already been mentioned—differes from that circular shape at least in places, so that the corner spaces or corner regions 115 are formed. Especially where the housing parts 101 and 102 have been rotated and/or moved apart axially, it is possible, according to FIG. 21, in which some parts VG are shown rotated, for the air drawn in to be drawn in according to arrows Pf 1 and Pf 2 in FIG. 21 via those corner regions 115, which are then open, and to be conveyed via openings 116 close to the base 117 of the device body 102 and via at least one non-return valve 118—according to FIG. 15 two non-return valves 118—to the air channels 6a, 6b and 6c and to the metering rod 5.

Consequently it is at the same time possible for the end face of the outer wall 114 of the device body 102 containing the metering needle to rest, in the position in which the housing parts are pushed together, against a stop surface 119 of the other housing part 101 having a matching encircling shape, and for the airway to be cut off in that position and the interior of the inhaler I to be closed in an airtight manner. The shutting off of the air from the air channels 6a, 6b and 6c and from the metering region is therefore not dependent solely upon the return force of the return flap or the non-return valve R but, in the position in which the housing parts are pushed together, the airway is additionally closed in an airtight manner.

The rotary movement, which according to the invention can be converted into the axial metering movement, also permits monitoring and indication of the metering operations that have already been carried out, instead of using a counter 7. In the embodiments according to FIGS. 14 to 30, one housing part contains an indicator ring 121 which is rotatable relative to an indicator window 120 and which can be advanced by a small angular amount of the same size and—in view of the rotary metering movement, which is always to be carried out in the same direction—in the same direction as a result of the rotation of the two housing parts 101 and 102 relative to each other when metering is carried out. The exact design and arrangement of such an indicator device is shown in FIGS. 22 to 28.

It will be seen from those Figures that the indicator ring 121 is in the form of a toothed wheel which is mounted eccentrically with respect to an internally toothed wheel 122 having a concave or internal toothing in the housing part or device body 102 having the metering needle 5, and the external toothing of which fits into the internal toothing of that internally toothed wheel 122 which is firmly joined to the mentioned housing part 102. The number of teeth on the inner toothed wheel acting as the indicator ring 121 differs from the number of teeth on the internally toothed wheel 122 by such a small amount, i.e. is smaller by such a small number, that the inner toothed wheel is rotatable relative to the internally toothed wheel 122 by approximately a single revolution or a fraction thereof when a given number of metering operations, for example from 100 to 200, has been carried out. FIGS. 23 to 28 show that the teeth of the indicator ring 121 are each visible from the outside in the indicator window 120, especially when the indicator window is clear or transparent and the indicator ring 121 is suitably coloured. The colour may vary over the circumference of the indicator ring 121 in order to indicate how metering is progressing or how the storage chamber 4 is emptying.

The manner in which indication is carried out as a result of the rotation of the device body 102 relative to the housing part 101 several times by a quarter of a revolution, and the advancement of the indicator ring 121, are shown in FIGS. 24 to 28 by marking one of the teeth of the indicator ring 121. At the same time, those Figures also show that the indicator ring 121, and hence the metering movement, can be blocked once the given number of metering operations has been reached.

Figure 24:
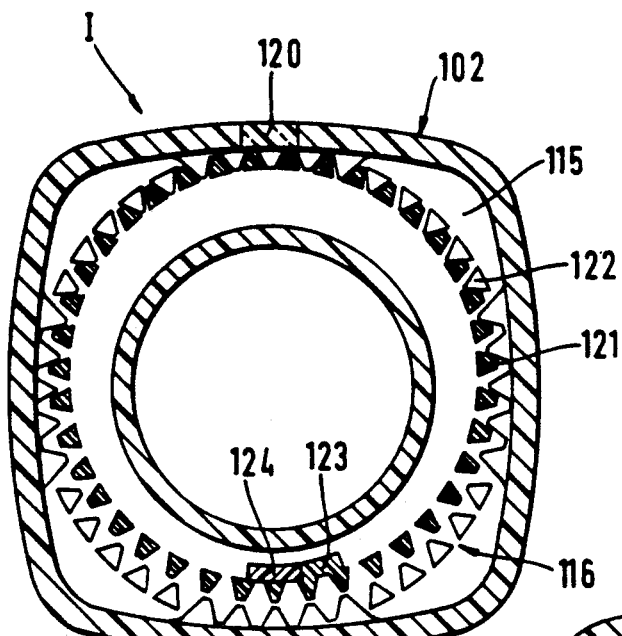
FIG. 24 to FIG. 28 show the indicator device according to FIG. 23 in various positions after an increasing number of metering operations, FIG. 28 showing blocking after the given maximum number of metering operations.
Figure 25:
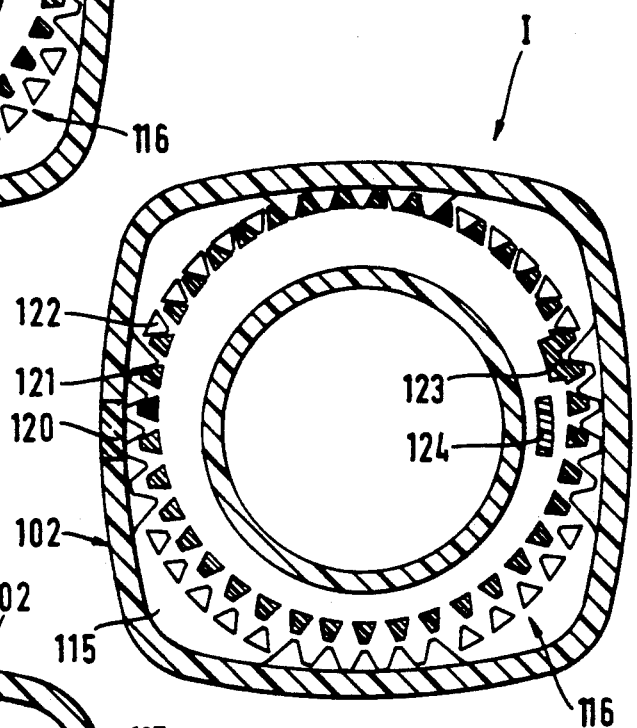

While FIG. 24 shows the state of the inhaler I as supplied and the marked tooth is located at one side of the indicator window 120, FIG. 25 shows a first metering operation, in which the device body 102 having the indicator window 120 has been rotated through 90 degrees. Accordingly, the indicator ring 121 is also advanced via the toothing. Subsequently there follow the axial return movement and further metering operations, FIG. 26, for example, showing the position after the fourth metering operation. The marked tooth has now covered approximately the width of the indicator window 120.

The important fact here is that the metering movement will be blocked after a given number of metering operations, in this case, for example, 200 metering operations, as has already been mentioned.

Figure 26:
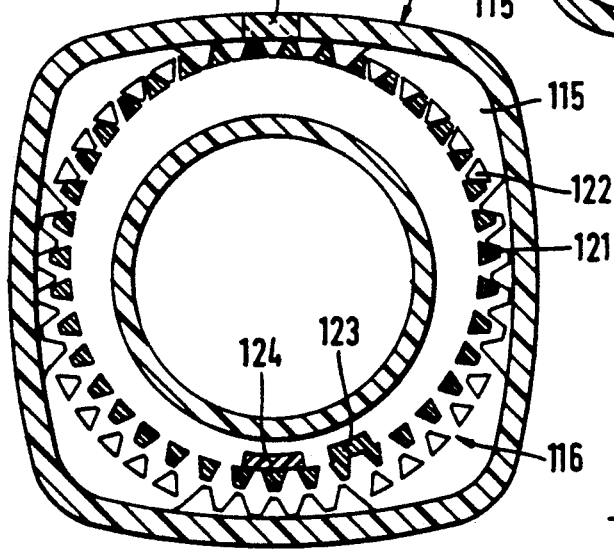
Figure 27:
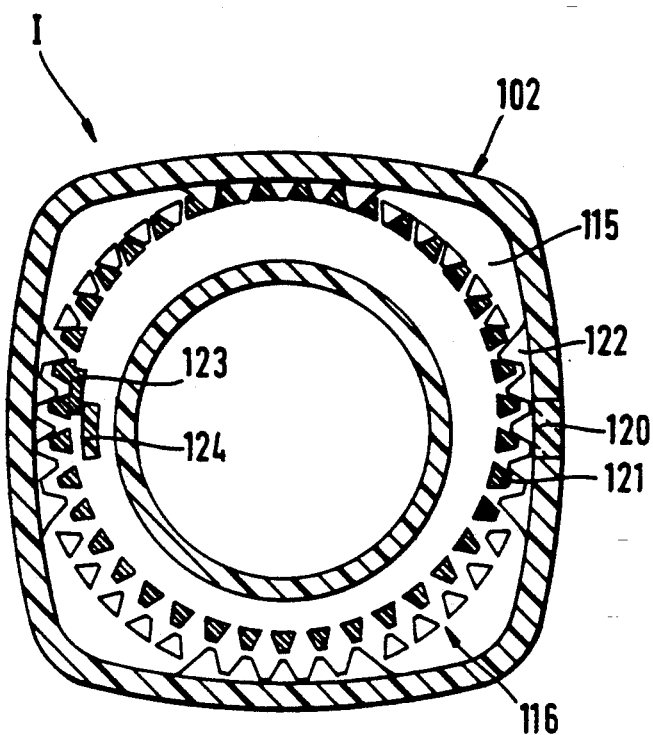

This blocking is effected by means of the indicator ring 121 as follows: the toothed wheel acting as the indicator ring 121 has on its inner side remote from the teeth a stop 123 which cooperates with a counter-stop 124 on the housing part 101, which is rotatable relative to the indicator ring, in such a manner that the two stops 123 and 124 are close to or even touch each other in the initial position according to FIG. 24 and, according to FIGS. 25 to 27, can gradually be moved in the circumferential direction, as a result of the metering movements, first away from each other and then towards each other again, the two stops 123 and 124 moving into two planes that are offset vertically relative to each other as a result of the simultaneous axial displacement, and then returning to a common plane or to approximately the same level as a result of the return movement. At the same time, the eccentric arrangement ensures that, as shown in FIG. 27, the two stops still do not collide with each other even after a relatively large number of metering operations, for example after the last metering operation (e.g. after 197 metering operations).

Figure 28:
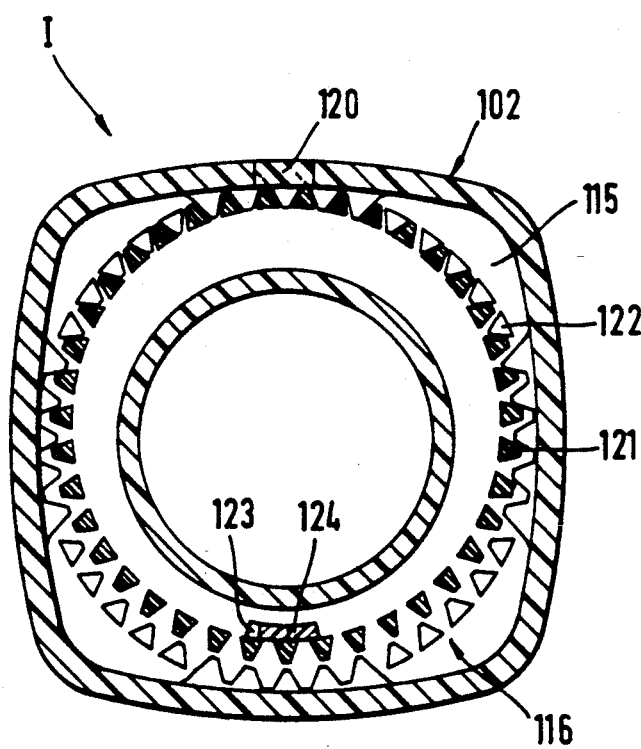

FIG. 28 shows that, after approximately one revolution of the indicator ring 121 and after the last metering operation, the two stops 123 and 124 lie above each other in the two planes in such a manner that the axial return movement into the initial position of the inhaler according to FIG. 14 and therefore a further metering operation starting from that position are prevented (blocking is effective). The rotary movement that is used for the metering operation can therefore not only be used at the same time in an advantageous manner for rotating an indicator ring, but that indicator ring can acquire an additional function with the aid of the stops 123 and 124, namely to lock the inhaler I after a given number of metering operations. It is thus possible to prevent the user from continuing to carry out metering operations, and receiving insufficient amounts of solids, when the inhaler I is substantially empty.

Figure 29:
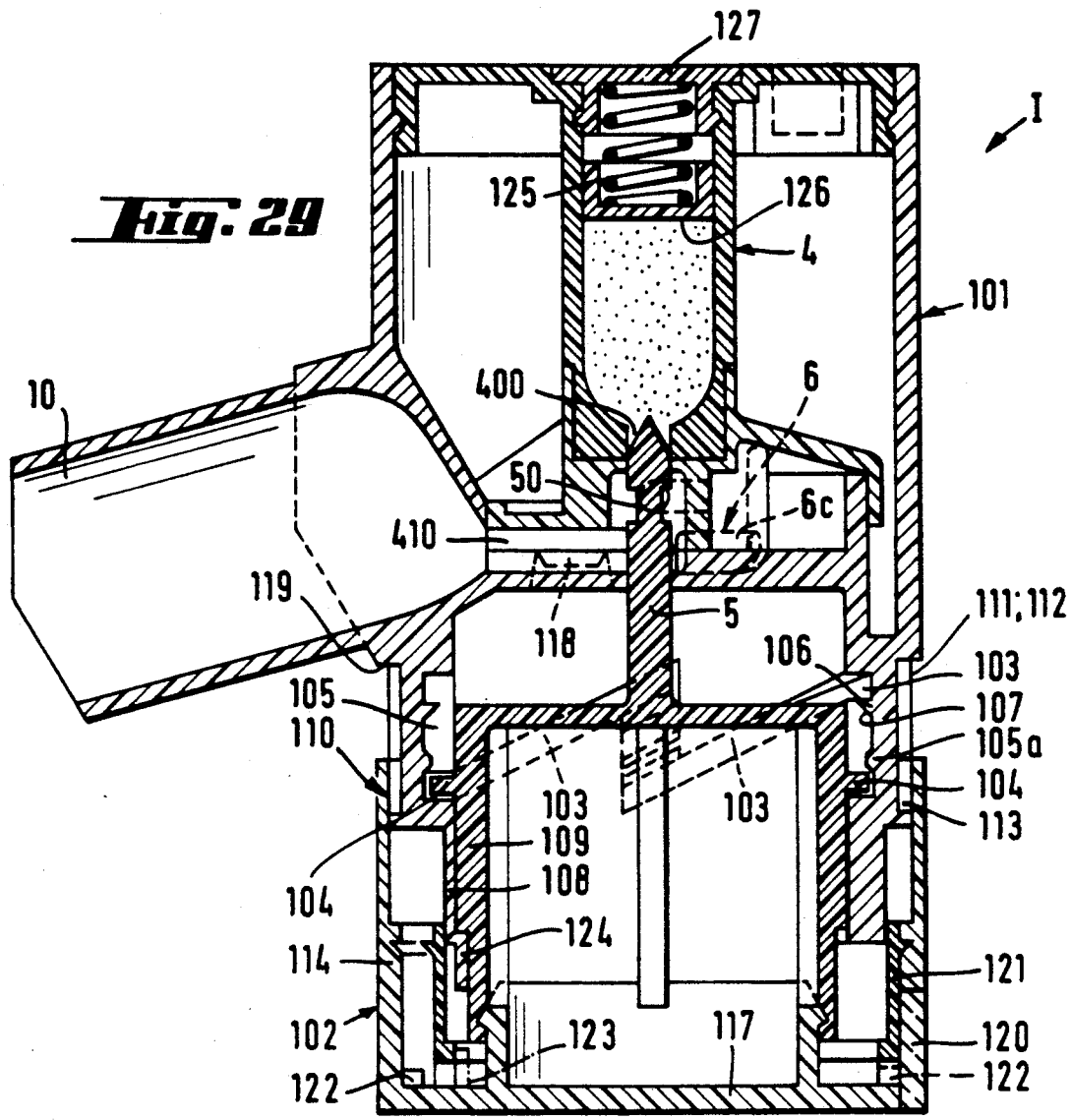
FIG. 29 is a longitudinal section of a modified inhaler in the second relative position, there being provided in the storage chamber a spring-loaded piston which follows the movement of the solids in the storage chamber.
Figure 30:
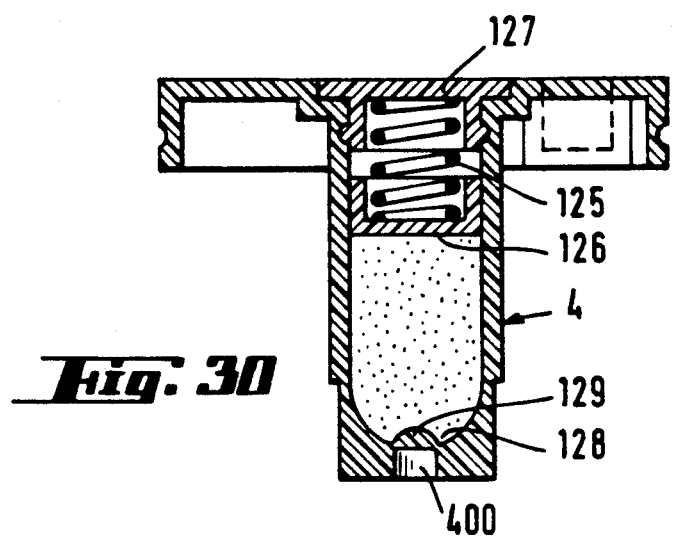
FIG. 30 is a longitudinal section through a replaceable storage chamber having a closure which is closed by means of predetermined breaking points or the like and can be opened automatically by means of the metering rod by insertion into the inhaler, a spring-loaded following piston likewise being provided in this embodiment.

FIGS. 29 and 30 show embodiments of the inhaler I according to the invention in which the above-mentioned features and measures are likewise fulfilled, but in which there is additionally arranged in the storage chamber 4, at the end remote from the metering rod 5, a piston 126 which is acted upon by a weak spring 125, in this case a helical spring, and which moves with the contents of the storage chamber 4 as the latter empties. The strength of the spring is sufficiently slight that the solids are not compressed, but at the same time it is sufficiently strong that the spring is able to push the piston 126 against the weight of the solids and against the piston's own weight, so that it moves with the contents of the chamber as the latter empties. The entire inhaler I can therefore be used in virtually any position, i.e. the user can even use it while lying down, without having to adopt a difficult position, and it is nevertheless ensured that with each metering movement the user is able to inhale the amount of solids corresponding to the volume of the metering recess 50.

These Figures, and especially FIG. 30, also show that the storage chamber 4 may be arranged inside the housing part 101 in such a manner that it can be removed and replaced, and/or it may have a removable cover 127. Consequently, when the storage chamber 4 is empty, only the storage chamber and not the entire inhaler I needs to be replaced, or the storage chamber may be refilled. The amount of waste is correspondingly small.

FIG. 30 also shows that the storage chamber 4 arranged replaceably in the housing part 101 has, in the initial state prior to assembly, a closure 129 for the passageway 400 for the metering rod 5, which closure 129 can be pierced, pushed out and/or is fastened in an air-tight manner by means of predetermined breaking points 128 and which can automatically be pushed in and opened by the metering rod 5 on insertion of the storage chamber 4 into its housing part 101. The replacement of a substantially empty metering chamber 4 with a full metering chamber 4 is therefore very simple because, at the same time as the metering chamber 4 is inserted into the use position, the connection with the airway is made and the metering rod 5 moves into its first metering position.

In this connection it is possible for the closure 129 of the storage chamber 4, which closure 129 is opened as a result of assembly, to be pivotable into the interior of the storage chamber 4, i.e. to remain joined to the wall of the storage chamber 4, and its diameter is in that case advantageously greater than the axial extent of the metering recess 50 so that the latter is able to slide past the inwardly pivoted closure 129 without difficulty.

As has already been mentioned, the inhaler according to the invention has a number of advantages. Safe, quick, reliable and complete filling of the metering recess is ensured, so that the metered amount of solids is very constant and a user who is having difficulty in breathing can quickly and reliably inhale a specific amount of powder providing relief. Moreover, the inhaler is especially suitable for the inhalation of small-grained and therefore poorly flowable powders. In addition, the penetration of moisture into the inhaler, and thus the formation of lumps in the powder, is avoided. Furthermore, with the inhaler according to the invention the powder may, as has been described, be stored in a capsule, so that it is even possible to use powders whose pharmaceutical activity decreases on permanent contact with the air (direct storage in the storage chamber) (see, for example, the construction according to FIG. 30). The inhaler is easily taken apart and cleaned, is simple to use and also is not designed as a disposable inhaler. It is especially suitable for the inhalation of substances and mixtures of substances having anti-asthmatic activity, very especially for the inhalation of a mixture of formoterol and lactose. The device is especially simple to use if the axial metering movement is produced by partial rotation of the two housing parts 101 and 102 relative to each other, because such a rotation can be carried out considerably more reliably by a user than can a relatively short, purely axial movement which is made more difficult by frictional forces.

The inhaler I for introducing a metered amount of solids, for example pharmaceutically active powders, into a stream of air drawn in by a user comprises a storage chamber 4 into which a metering rod 5 extends. The metering rod 5 is provided with a metering recess 50 which fixes the amount of solids to be mixed with the air stream. The storage chamber 4 and the metering rod 5 are movable relative to each other in such a manner that in a first relative position of the metering rod 5 and the storage chamber 4 the metering recess 50 of the metering rod 5 is located in the storage chamber 4, where it is filled with solids, and in a second relative position it is located in the air channel, where the solids are mixed with the air stream. The axial relative movement can be brought about by the rotation of two housing parts 101, 102 over sloping surfaces 103.

What is claimed is:

1. An inhaler for introducing a metered amount of pharmaceutically active powder or mixture of pharmaceutically active powders into a stream of air which is drawn in by a user, said stream of air and the pharmaceutically active powder or mixture of pharmaceutically active powders forming a powder/air mixture, said inhaler comprising:
   a device body;
   a storage chamber for storing the powder;
   an air inlet;
   an outlet for the powder/air mixture;
   an air channel connecting said air inlet with said outlet for the powder/air mixture;
   a metering rod provided with a recess to measure a fixed amount of powder and to introduce said fixed amount of powder into said stream of air;
   a locking device; and
   an unlocking element;
   said storage chamber including a first opening through which said metering rod enters the storage chamber;
   said metering rod extending axially into said storage chamber through the first opening in said storage chamber;
   said storage chamber and said metering rod being movable relative to each other such that, in a first relative position said recess of said metering rod is located in said storage chamber and in a second relative position said recess is located in said air channel; said locking device holding said storage chamber and said metering rod in said first relative position; and
   said unlocking element releasing the locking device.

2. An inhaler according to claim 1 further comprising an operating member; and
   a return spring;
   said storage chamber further provided with an extension having a second opening;
   said extension closing said air channel in said first relative position;
   said second opening opening said air channel in said second relative position;
   said operating member further provided with a vibration means;
   said vibration means exercising vibrations on said storage chamber when said storage chamber is in said first relative position;
   said vibration means comprising a snap spring.

3. An inhaler according to claim 1, further being provided with a separatable suction piece comprising at least a part of said air channel as well as an outlet of said inhaler, said part of said air channel having a cross-section that widens towards said outlet.

4. An inhaler according to claim 3, further comprising a separate closing cap which is adapted to fit onto said suction piece.

5. An inhaler according to claim 4, wherein a drying agent is provided in said closing cap.

6. An inhaler according to claim 1, wherein a one-way valve is provided at said air inlet.

7. An inhaler according to claim 1, further being provided with a resettable counter which is incremented when the first relative position of said metering rod and said storage chamber is reached.

8. An inhaler according to claim 1, wherein the solids comprise a pharmaceutically effective antiasthmatic substance.

9. An inhaler according to claim 8, wherein said pharmaceutically effective antiasthmatic substance is a mixture of formoterol and lactose.

10. An inhaler for introducing a metered amount of pharmaceutically active powder or mixture of pharmaceutically active powders into a stream of air which is drawn in by a user, said stream of air and the pharmaceutically active powder or mixture of pharmaceutically active powders forming a powder/air mixture, said inhaler comprising:
    a device body;
    a storage chamber for storing the powder;
    an air inlet;
    an outlet for the powder/air mixture;
    an air channel connecting said air inlet with said outlet for the powder/air mixture;
    a metering rod provided with a recess to measure a fixed amount of powder and to introduce said fixed amount of powder into said stream of air;
    said storage chamber including an opening through which said metering rod enters the storage chamber;
    said metering rod extending axially into said storage chamber through the opening in said storage chamber;
    said storage chamber and said metering rod being movable relative to each other such that, in a first relative position said recess of said metering rod is located in said storage chamber and in a second relative position said recess is located in said air channel;

wherein said device body carries said metering rod, further comprising a housing part containing said storage chamber, said housing part and said device body being displaceable relative to each other from said first relative position of said storage chamber and said metering rod, upon axially pushing together said housing part and said device body, to said second relative position, upon axially moving apart said housing part and said device body;

wherein said housing part and said device body are rotatable relative to each other; wherein at least one sloping surface is provided on said housing part or on said device body; wherein at least one counter-member is provided on the sloping surface;

wherein the counter-member is guided on said sloping surface thereby converting the rotary movement of said housing part and said device body relative to each other into an axial movement.

11. An inhaler according to claim 10, wherein said housing part or said device body is provided with a plurality of sloping surfaces, wherein each sloping surface of said plurality of sloping surfaces has an equal gradient and equal length over its periphery; and wherein said device body or said housing part respectively, is provided with a plurality of counter-members, said plurality of counter-members being guided on said plurality of sloping surfaces.

12. An inhaler according to claim 10, wherein four sloping surfaces are provided which extend over almost 90 degrees, said sloping surfaces being arranged level with one another and ascending in the same direction to final positions, and further wherein four corresponding projections are provided as counter-members to said four sloping surfaces, which are guided on said sloping surfaces, and wherein there are provided vertically oriented openings, return grooves or the like at the final positions of said sloping surfaces, in which said projections can slide back, so that said housing part containing said storage chamber and said device body carrying said metering rod can be pushed together to said first relative position.

13. An inhaler according to claim 12, wherein each of said return grooves is provided with a cam-like projection, over which each of said counter-members is displaceable, and further wherein in said return grooves there is provided at least one saw tooth projection having an inclined side and a vertically extending side, said vertically extending side being aligned with said sloping surface for said counter-members, said counter-members being axially displaceable over said inclined side of said saw tooth projection and being located behind said vertically extending side when said housing part and said device body are pushed together to said first relative position.

14. An inhaler according to claim 12, wherein said sloping surfaces are shaped as grooves, each corresponding to a sector of a screw thread, said grooves being arranged on an inside wall portion of said housing part.

15. An inhaler according to claim 10, further comprising a locking mechanism, a ratchet or the like, which is arranged at respective contact points between said housing part and said device body, which are rotatable relative to each other, said locking mechanism, ratchet or the like permitting a rotational movement of said housing part and said device body relative to each other in one rotational direction only.

16. An inhaler according to claim 15, wherein said locking mechanism comprises a ratchet wheel, said ratchet wheel comprising saw teeth; said saw teeth located on said housing part or on said device body, said saw teeth spaced at equal intervals, said ratchet wheel further comprising counter-teeth or groups of counter-teeth; said counter-teeth or groups of counter-teeth located on said device body or on said housing part, said locking mechanism further provided with catch intervals, wherein said counter-teeth are at an offset relative to one another in a circumferential direction, said offset of said counter-teeth relative to one another being so selected, that the catch intervals of said locking mechanism are smaller than the equal intervals.

17. An inhaler according to claim 16, wherein said saw teeth, said equal intervals between said saw teeth, and said counter-teeth are arranged along a circumference of said housing part or of said device body, respectively, and extend in an axial direction.

18. An inhaler according to claim 16, wherein said device body carrying said metering rod is at least partially provided with a double wall having an inner wall and an outer wall, wherein said counter-members are arranged along said inner wall of said double wall to project radially outward from said inner wall and cooperate with said sloping surfaces on said housing part, and wherein said outer wall of said double wall of said device body is arranged relative to the housing part such that it encloses a wall portion of said housing part which is provided with said sloping surfaces, and further wherein said outer wall of said double wall carries the counter-teeth for said ratchet wheel, said outer wall arranged on the outside of said housing part.

19. An inhaler according to claim 18, wherein said inner wall of said double wall of said device body and said wall portion of said housing part which is provided with said sloping surfaces, have a circular shape, and wherein at least a portion of said outer wall of said device body has a cross-section that differs from said circular shape such, that corner regions are formed between said walls, and further wherein, when air is drawn in through said corner regions, particularly after said housing part and said device body have been rotated relative to each other and/or have been moved apart from each other axially, said air is guided via openings, that are arranged near the base of said device body, and via at least one one-way valve to said air channel and to said metering rod.

20. An inhaler according to claim 18, wherein said outer wall of said device body is provided with an end face and said housing part is provided with a corresponding stop surface, and wherein in said first relative position, after said device body and said housing part have been pushed together, said end face rests against said stop surface thereby preventing the entering of any air and closing the interior of said inhaler in an airtight manner.

21. An inhaler according to claim 20, wherein said housing part and said device body, respectively, comprise an indicator ring and an indicator window, said indicator ring being rotated a small angular amount relative to said indicator window each time a metering operation is carried out.

22. An inhaler according to claim 21, wherein the rotational movement of said indicator ring and therefore the metering operation is blocked once a given maximum number of metering operations has been reached.

23. An inhaler according to claim 21, wherein said device body is provided with a gear wheel or an internal gearing, and wherein said indicator ring comprises a circumferential gearing, said indicator ring comprising said circumferential gearing being mounted eccentrically with respect to said internal gearing on said device body, the circumferential gearing of said indicator ring and the internal gearing or the gear wheel of said device body interlocking in a respective contact region, said circumferential gearing of said indicator ring and said internal gearing or said gear wheel of said device body each having a number of teeth, wherein the number of teeth of the circumferential gearing slightly differs from the number of teeth of the internal gearing or the gear wheel such, that said indicator ring has a rotational movement relative to said device body of 360° or less when a given number of metering operations have been carried out.

24. An inhaler according to claim 23, wherein said indicator ring is provided with a stop and wherein said housing part is provided with a corresponding counter-stop, said stop and said corresponding counter-stop being located in a common plane in close vicinity to each other or touching each other prior to a first metering operation of the inhaler, said stop and said corresponding counter-stop moving apart along a generally circular path as an increasing number of metering operations is carried out, said stop and said corresponding counter-stop movable into two planes which are vertically offset relative to each other when said housing and said device body are rotated relative to each other and simultaneously are axially displaced relative to each other during a metering operation, and said stop and said corresponding counter-stop returning to said common plane when said housing part and said device body are pushed together axially, the arrangement of said stop and said corresponding counter-stop being such, that they come to lie above each other after the maximum number of metering operations has been carried out, thereby preventing said housing part and said device body from being pushed together again.

25. An inhaler according to claim 10, further comprising:
 a piston and
 a weak spring;
 said piston being housed in said storage chamber;
 said piston moving with said solids in said storage chamber as the storage chamber empties;
 said weak spring sufficiently weak to prevent compression of said powder contained in said storage chamber;
 said weak spring being sufficiently strong to push said piston against the weight of said powder and against the weight of said piston.

26. An inhaler according to claim 10, wherein said storage chamber is arranged inside said housing part, said storage chamber being removable and replaceable.

27. An inhaler according to claim 26, further comprising a closure; said closure provided for the passageway of said metering rod, said closure being pierceable, said closure having predetermined breaking points, said closure opening automatically upon insertion of said storage chamber into said housing part.

28. An inhaler according to claim 10, wherein said storage chamber is provided with a removable cover.

* * * * *